US012691213B2

(12) United States Patent
Grygus et al.

(10) Patent No.: US 12,691,213 B2
(45) Date of Patent: Jul. 28, 2026

(54) MEDICAL DEVICE PACKAGING AND RELATED METHODS

(71) Applicant: Regeneron Pharmaceuticals, Inc., Tarrytown, NY (US)

(72) Inventors: Bryan C. Grygus, Clifton Park, NY (US); Jim Fedor, Bayport, MN (US); Wayne Phillips, Hudson, WI (US); Anne Wespetal, Menomonie, WI (US); Ashley Johannes, Halfmoon, NY (US); Tanya Magana, Richmond, WI (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/744,094

(22) Filed: Jun. 14, 2024

(65) Prior Publication Data

US 2024/0416028 A1     Dec. 19, 2024

Related U.S. Application Data

(60) Provisional application No. 63/508,812, filed on Jun. 16, 2023.

(51) Int. Cl.
*A61M 5/00*          (2006.01)
(52) U.S. Cl.
CPC ................................. *A61M 5/002* (2013.01)
(58) Field of Classification Search
CPC .................................................... A61M 5/002
USPC ................................................ 206/364, 365
See application file for complete search history.

(56) References Cited

U.S. PATENT DOCUMENTS

| | | | |
|---|---|---|---|
| 2,459,304 | A | 1/1949 | Frederick et al. |
| 3,136,313 | A | 6/1964 | Enstrom et al. |
| 3,340,671 | A | 9/1967 | Loo |
| 3,342,180 | A | 9/1967 | Roland et al. |
| 3,507,386 | A | 4/1970 | Ishii et al. |
| 3,605,744 | A | 9/1971 | Dwyer et al. |
| 3,872,992 | A | 3/1975 | Larson |
| 3,916,894 | A | 11/1975 | Cloyd |

(Continued)

FOREIGN PATENT DOCUMENTS

| | | |
|---|---|---|
| AU | 1999018289 A1 | 9/1999 |
| AU | 2002301321 B2 | 6/2005 |

(Continued)

OTHER PUBLICATIONS

International Search Report and Written Opinion mailed Aug. 26, 2024 in International Application No. PCT/US2024/029782, 13 pages.

(Continued)

*Primary Examiner* — Jacob K Ackun
(74) *Attorney, Agent, or Firm* — Bookoff McAndrews, PLLC

(57)          ABSTRACT

A packaging comprising a tray having a body surrounding an exposed cavity and a groove; a lip surrounding the opening, wherein the lip extends radially outward from the cavity and defines a periphery of the tray; a retainer for covering a portion of the opening of the tray, the retainer having an aperture, wherein the aperture corresponds to the groove of the tray; a removable cover; and an auto-injector contained within the cavity, wherein the auto-injector is pre-filled with a medicament or other fluid.

20 Claims, 12 Drawing Sheets

(56) References Cited

U.S. PATENT DOCUMENTS

| | | | |
|---|---|---|---|
| 4,187,861 A | 2/1980 | Heffernan | |
| 4,244,287 A | 1/1981 | Maffet | |
| 4,396,385 A | 8/1983 | Kelly et al. | |
| 4,397,903 A | 8/1983 | Allen et al. | |
| 4,410,323 A | 10/1983 | Hodosh et al. | |
| 4,548,601 A | 10/1985 | Lary | |
| 4,624,660 A | 11/1986 | Mijers et al. | |
| 4,703,781 A | 11/1987 | Meyer et al. | |
| 4,808,169 A | 2/1989 | Haber et al. | |
| 4,973,504 A | 11/1990 | Romberg et al. | |
| 4,997,423 A | 3/1991 | Okuda et al. | |
| 5,009,646 A | 4/1991 | Sudo et al. | |
| 5,073,169 A | 12/1991 | Raiken | |
| 5,088,996 A | 2/1992 | Kopfer et al. | |
| 5,180,371 A | 1/1993 | Spinello | |
| 5,220,948 A | 6/1993 | Haber et al. | |
| 5,279,606 A | 1/1994 | Haber et al. | |
| 5,288,560 A | 2/1994 | Sudo et al. | |
| 5,322,515 A | 6/1994 | Karas et al. | |
| 5,334,179 A | 8/1994 | Poli et al. | |
| 5,354,287 A | 10/1994 | Wacks | |
| 5,372,787 A | 12/1994 | Ritter | |
| 5,382,235 A | 1/1995 | Sak | |
| 5,466,220 A | 11/1995 | Brenneman | |
| 5,487,732 A | 1/1996 | Jeffrey | |
| 5,514,116 A | 5/1996 | Vaillancourt et al. | |
| 5,690,618 A | 11/1997 | Smith et al. | |
| 5,814,020 A | 9/1998 | Gross | |
| 5,858,001 A | 1/1999 | Tsals et al. | |
| 5,873,860 A | 2/1999 | Kahlert | |
| 5,902,276 A | 5/1999 | Namey, Jr. | |
| 5,951,527 A | 9/1999 | Sudo | |
| 6,003,566 A | 12/1999 | Thibault et al. | |
| 6,003,736 A | 12/1999 | Ljunggren | |
| 6,004,300 A | 12/1999 | Butcher et al. | |
| 6,022,339 A | 2/2000 | Fowles et al. | |
| 6,074,369 A | 6/2000 | Sage et al. | |
| 6,090,070 A | 7/2000 | Hager et al. | |
| 6,090,081 A | 7/2000 | Sudo et al. | |
| 6,123,991 A | 9/2000 | Spallek et al. | |
| 6,129,712 A | 10/2000 | Sudo et al. | |
| 6,142,977 A | 11/2000 | Kolberg et al. | |
| 6,149,614 A | 11/2000 | Dunshee et al. | |
| 6,162,200 A | 12/2000 | Sawa et al. | |
| 6,165,155 A | 12/2000 | Jacobsen et al. | |
| 6,171,276 B1 | 1/2001 | Lippe et al. | |
| 6,189,580 B1 | 2/2001 | Thibault et al. | |
| 6,238,367 B1 | 5/2001 | Christiansen et al. | |
| 6,277,095 B1 | 8/2001 | Kriesel et al. | |
| 6,346,095 B1 | 2/2002 | Gross et al. | |
| 6,364,865 B1 | 4/2002 | Lavi et al. | |
| 6,378,576 B2 | 4/2002 | Thibault et al. | |
| 6,478,771 B1 | 11/2002 | Lavi et al. | |
| 6,479,916 B1 | 11/2002 | Bobay et al. | |
| 6,500,150 B1 | 12/2002 | Gross et al. | |
| 6,511,459 B1 | 1/2003 | Fago | |
| 6,547,755 B1 | 4/2003 | Lippe et al. | |
| 6,585,693 B1 | 7/2003 | Dischler | |
| 6,595,956 B1 | 7/2003 | Gross et al. | |
| 6,641,565 B1 | 11/2003 | Lavi et al. | |
| 6,645,181 B1 | 11/2003 | Lavi et al. | |
| 6,681,946 B1 | 1/2004 | Jansen et al. | |
| 6,689,108 B2 | 2/2004 | Lavi et al. | |
| 6,723,068 B2 | 4/2004 | Lavi et al. | |
| 6,799,612 B2 | 10/2004 | Stewart et al. | |
| 6,817,990 B2 | 11/2004 | Yap et al. | |
| 6,824,529 B2 | 11/2004 | Gross et al. | |
| 6,837,876 B2 | 1/2005 | Bally et al. | |
| 6,843,782 B2 | 1/2005 | Gross et al. | |
| 6,913,591 B2 | 7/2005 | Itoh et al. | |
| 6,939,324 B2 | 9/2005 | Gonnelli et al. | |
| 6,945,417 B2 | 9/2005 | Jansen et al. | |
| 7,001,360 B2 | 2/2006 | Veasey et al. | |
| 7,004,928 B2 | 2/2006 | Aceti et al. | |
| 7,195,609 B2 | 3/2007 | Huegli | |
| 7,250,037 B2 | 7/2007 | Shermer et al. | |
| 7,294,752 B1 | 11/2007 | Propp | |
| 7,384,413 B2 | 6/2008 | Gross et al. | |
| 7,416,540 B2 | 8/2008 | Edwards et al. | |
| 7,455,663 B2 | 11/2008 | Bikovsky | |
| 7,481,792 B2 | 1/2009 | Gonnelli et al. | |
| 7,547,297 B2 | 6/2009 | Brinkhues | |
| 7,563,253 B2 | 7/2009 | Tanner et al. | |
| D602,155 S | 10/2009 | Foley et al. | |
| D602,586 S | 10/2009 | Foley et al. | |
| 7,628,770 B2 | 12/2009 | Ethelfeld | |
| 7,648,482 B2 | 1/2010 | Edwards et al. | |
| 7,648,483 B2 | 1/2010 | Edwards et al. | |
| 7,674,246 B2 | 3/2010 | Gillespie et al. | |
| 7,678,072 B2 | 3/2010 | Weber | |
| 7,678,079 B2 | 3/2010 | Shermer et al. | |
| 7,691,308 B2 | 4/2010 | Brinkhues | |
| 7,727,202 B2 | 6/2010 | Kirchhofer et al. | |
| 7,731,686 B2 | 6/2010 | Edwards et al. | |
| 7,731,690 B2 | 6/2010 | Edwards et al. | |
| 7,749,194 B2 | 7/2010 | Edwards et al. | |
| 7,749,202 B2 | 7/2010 | Miller et al. | |
| 7,766,873 B2 | 8/2010 | Moberg et al. | |
| 7,766,882 B2 | 8/2010 | Sudo et al. | |
| 7,780,636 B2 | 8/2010 | Radmer et al. | |
| 7,883,660 B2 | 2/2011 | Matsuda et al. | |
| 7,892,199 B2 | 2/2011 | Mhatre et al. | |
| 7,892,206 B2 | 2/2011 | Moberg et al. | |
| 7,909,796 B2 | 3/2011 | Weber | |
| 7,918,823 B2 | 4/2011 | Edwards et al. | |
| 7,922,699 B2 | 4/2011 | Baba et al. | |
| 7,927,315 B2 | 4/2011 | Sudo et al. | |
| 7,947,017 B2 | 5/2011 | Edwards et al. | |
| 7,981,085 B2 | 7/2011 | Ethelfeld | |
| 7,988,675 B2 | 8/2011 | Gillespie, III et al. | |
| 7,993,301 B2 | 8/2011 | Boyd et al. | |
| 7,998,117 B2 | 8/2011 | Gross et al. | |
| 8,016,788 B2 | 9/2011 | Edwards et al. | |
| 8,021,344 B2 | 9/2011 | Edwards et al. | |
| 8,052,648 B2 | 11/2011 | Dikeman et al. | |
| 8,056,716 B2 * | 11/2011 | Fonteyne | B32B 15/08 |
| | | | 220/359.3 |
| 8,057,434 B2 | 11/2011 | Burroughs et al. | |
| 8,062,257 B2 | 11/2011 | Moberg et al. | |
| 8,065,096 B2 | 11/2011 | Moberg et al. | |
| 8,088,096 B2 | 1/2012 | Lauchard et al. | |
| 8,105,281 B2 | 1/2012 | Edwards et al. | |
| 8,123,719 B2 | 2/2012 | Edwards et al. | |
| 8,123,724 B2 | 2/2012 | Gillespie, III | |
| 8,147,460 B2 | 4/2012 | Etter et al. | |
| 8,162,898 B1 | 4/2012 | Wright | |
| 8,172,082 B2 | 5/2012 | Edwards et al. | |
| 8,172,804 B2 | 5/2012 | Bikovsky | |
| 8,182,447 B2 | 5/2012 | Moberg et al. | |
| 8,202,249 B2 | 6/2012 | Iio et al. | |
| 8,206,351 B2 | 6/2012 | Sugimoto et al. | |
| 8,206,360 B2 | 6/2012 | Edwards et al. | |
| 8,226,610 B2 | 7/2012 | Edwards et al. | |
| 8,226,615 B2 | 7/2012 | Bikovsky | |
| 8,231,573 B2 | 7/2012 | Edwards et al. | |
| 8,240,468 B2 * | 8/2012 | Wilkinson | A61B 5/15003 |
| | | | 206/363 |
| 8,267,893 B2 | 9/2012 | Moberg et al. | |
| 8,287,500 B2 | 10/2012 | Baba et al. | |
| 8,298,171 B2 | 10/2012 | Ishikawa et al. | |
| 8,303,535 B2 | 11/2012 | Both et al. | |
| 8,303,549 B2 | 11/2012 | Mejlhede et al. | |
| 8,313,466 B2 | 11/2012 | Edwards et al. | |
| 8,348,898 B2 | 1/2013 | Cabiri | |
| 8,361,026 B2 | 1/2013 | Edwards et al. | |
| 8,361,027 B2 | 1/2013 | Gross et al. | |
| 8,361,028 B2 | 1/2013 | Gross et al. | |
| 8,361,029 B2 | 1/2013 | Edwards et al. | |
| D676,549 S | 2/2013 | Lovell et al. | |
| 8,376,985 B2 | 2/2013 | Pongpairochana et al. | |
| 8,409,141 B2 | 4/2013 | Johansen et al. | |
| 8,425,462 B2 | 4/2013 | Edwards et al. | |
| 8,433,383 B2 | 4/2013 | O'Neil et al. | |
| 8,444,604 B2 | 5/2013 | Cindrich et al. | |

(56) References Cited

U.S. PATENT DOCUMENTS

| | | | |
|---|---|---|---|
| 8,453,838 | B2 | 6/2013 | Hill |
| 8,460,244 | B2 | 6/2013 | Srisathapat et al. |
| 8,475,414 | B2 | 7/2013 | Boyd et al. |
| 8,512,287 | B2 | 8/2013 | Cindrich et al. |
| 8,512,288 | B2 | 8/2013 | Moberg et al. |
| 8,540,681 | B2 | 9/2013 | Hetherington |
| 8,544,645 | B2 | 10/2013 | Edwards et al. |
| 8,562,567 | B2 | 10/2013 | Gundberg |
| 8,603,027 | B2 | 12/2013 | Favreau |
| 8,603,045 | B2 | 12/2013 | Weber |
| 8,608,698 | B2 | 12/2013 | Edwards et al. |
| 8,617,110 | B2 | 12/2013 | Moberg et al. |
| 8,618,948 | B2 | 12/2013 | Oberli et al. |
| 8,627,816 | B2 | 1/2014 | Edwards et al. |
| 8,641,669 | B2 | 2/2014 | Renz et al. |
| 8,647,074 | B2 | 2/2014 | Moberg et al. |
| 8,647,296 | B2 | 2/2014 | Moberg et al. |
| 8,652,387 | B2 | 2/2014 | Etter et al. |
| 8,668,672 | B2 | 3/2014 | Moberg et al. |
| 8,668,675 | B2 | 3/2014 | Chase et al. |
| 8,668,972 | B2 | 3/2014 | Lewis et al. |
| 8,679,055 | B2 | 3/2014 | Ishikawa et al. |
| 8,679,395 | B2 | 3/2014 | Nagel et al. |
| 8,690,827 | B2 | 4/2014 | Edwards et al. |
| 8,690,836 | B2 | 4/2014 | Mathews et al. |
| 8,708,971 | B2 | 4/2014 | Segal |
| 8,715,237 | B2 | 5/2014 | Moberg et al. |
| 8,722,178 | B2 | 5/2014 | Ashmead et al. |
| 8,740,847 | B2 | 6/2014 | Levesque et al. |
| 8,742,032 | B2 | 6/2014 | Abe et al. |
| 8,748,544 | B2 | 6/2014 | Abe et al. |
| 8,771,239 | B2 | 7/2014 | Boyd et al. |
| 8,795,669 | B2 | 8/2014 | Walsh et al. |
| 8,808,244 | B2 | 8/2014 | Adlon et al. |
| 8,834,419 | B2 | 9/2014 | Jennings |
| 8,852,141 | B2 | 10/2014 | Mhatre et al. |
| 8,858,511 | B2 | 10/2014 | Gonnelli et al. |
| 8,864,739 | B2 | 10/2014 | Moberg et al. |
| 8,876,779 | B2 | 11/2014 | Johansen et al. |
| 8,900,201 | B2 | 12/2014 | Edhouse et al. |
| 8,900,205 | B2 | 12/2014 | Ishii |
| 8,915,882 | B2 | 12/2014 | Cabiri |
| 8,920,367 | B2 | 12/2014 | Edwards et al. |
| 8,920,374 | B2 | 12/2014 | Bokelman et al. |
| 8,920,377 | B2 | 12/2014 | Edwards et al. |
| 8,926,569 | B2 | 1/2015 | Bisegna et al. |
| 8,926,594 | B2 | 1/2015 | Edwards et al. |
| 8,939,935 | B2 | 1/2015 | O'Connor et al. |
| 8,939,943 | B2 | 1/2015 | Edwards et al. |
| D723,157 | S | 2/2015 | Clemente et al. |
| 8,945,056 | B2 | 2/2015 | Iio et al. |
| 8,956,331 | B2 | 2/2015 | Johansen et al. |
| 8,960,685 | B2 | 2/2015 | Maeda et al. |
| 8,961,469 | B2 | 2/2015 | Sonderegger et al. |
| 8,968,260 | B2 | 3/2015 | Horiuchi et al. |
| 8,974,413 | B2 | 3/2015 | Baba et al. |
| 8,992,478 | B2 | 3/2015 | Levesque |
| 8,998,842 | B2 | 4/2015 | Lauchard et al. |
| 9,011,371 | B2 | 4/2015 | Moberg et al. |
| 9,022,022 | B2 | 5/2015 | Edwards et al. |
| 9,024,768 | B2 | 5/2015 | Mandro et al. |
| 9,033,925 | B2 | 5/2015 | Moberg et al. |
| 9,039,664 | B2 | 5/2015 | Ogawa et al. |
| 9,056,170 | B2 | 6/2015 | Edwards et al. |
| 9,072,839 | B2 | 7/2015 | Kouyoumjian et al. |
| 9,078,976 | B2 | 7/2015 | Boyd et al. |
| 9,084,849 | B2 | 7/2015 | Edwards et al. |
| 9,101,706 | B2 | 8/2015 | Gonnelli et al. |
| 9,107,996 | B2 | 8/2015 | Brüggemann et al. |
| 9,107,999 | B2 | 8/2015 | Moberg et al. |
| 9,108,012 | B2 | 8/2015 | Pryce et al. |
| 9,114,213 | B2 | 8/2015 | Murakami et al. |
| 9,132,231 | B2 | 9/2015 | Gross et al. |
| D741,995 | S | 10/2015 | Prasser et al. |
| 9,149,575 | B2 | 10/2015 | Cabiri |
| 9,149,578 | B2 | 10/2015 | Byerly et al. |
| 9,149,579 | B2 | 10/2015 | Edwards et al. |
| 9,149,582 | B2 | 10/2015 | Sugimoto et al. |
| 9,155,844 | B2 | 10/2015 | Brereton et al. |
| 9,162,427 | B2 | 10/2015 | Nakano et al. |
| 9,173,880 | B2 | 11/2015 | Dix et al. |
| 9,173,999 | B2 | 11/2015 | Edwards et al. |
| 9,180,244 | B2 | 11/2015 | Anderson et al. |
| D745,142 | S | 12/2015 | O'Connor et al. |
| 9,238,108 | B2 | 1/2016 | Edwards et al. |
| 9,242,047 | B2 | 1/2016 | Brereton et al. |
| 9,254,373 | B2 | 2/2016 | Hørdum |
| 9,259,531 | B2 | 2/2016 | Kamen et al. |
| 9,259,539 | B2 | 2/2016 | Edwards et al. |
| 9,265,892 | B2 | 2/2016 | Segal |
| 9,278,177 | B2 | 3/2016 | Edwards et al. |
| 9,278,182 | B2 | 3/2016 | Edwards et al. |
| 9,297,370 | B2 | 3/2016 | Bruggemann et al. |
| 9,308,329 | B2 | 4/2016 | Boyd et al. |
| 9,327,073 | B2 | 5/2016 | Moberg et al. |
| 9,327,077 | B2 | 5/2016 | Edwards et al. |
| 9,339,605 | B2 | 5/2016 | Wimpenny et al. |
| 9,344,024 | B2 | 5/2016 | Favreau |
| 9,345,837 | B2 | 5/2016 | Horiuchi et al. |
| 9,352,090 | B2 | 5/2016 | Brereton et al. |
| 9,352,091 | B2 | 5/2016 | Edwards et al. |
| 9,364,606 | B2 | 6/2016 | Cindrich et al. |
| 9,364,608 | B2 | 6/2016 | Moberg et al. |
| 9,364,612 | B2 | 6/2016 | Hanson et al. |
| 9,375,529 | B2 | 6/2016 | Searle et al. |
| 9,375,532 | B2 | 6/2016 | Brereton et al. |
| 9,408,984 | B2 | 8/2016 | Durack et al. |
| 9,408,985 | B2 | 8/2016 | Cronenberg et al. |
| 9,415,169 | B2 | 8/2016 | Tachikawa et al. |
| D767,120 | S | 9/2016 | Tyce et al. |
| 9,433,732 | B2 | 9/2016 | Moberg et al. |
| 9,452,264 | B2 | 9/2016 | Maeda et al. |
| D768,288 | S | 10/2016 | O'Connor et al. |
| 9,463,280 | B2 | 10/2016 | Cabiri |
| 9,468,586 | B2 | 10/2016 | Kvale |
| 9,474,869 | B2 | 10/2016 | Edwards et al. |
| 9,480,793 | B2 | 11/2016 | Mhatre et al. |
| 9,492,610 | B2 | 11/2016 | Cabiri |
| 9,492,618 | B2 | 11/2016 | Day |
| 9,504,793 | B2 | 11/2016 | Eggert et al. |
| D774,640 | S | 12/2016 | Tyce et al. |
| 9,511,189 | B2 | 12/2016 | O'Connor et al. |
| 9,522,231 | B2 | 12/2016 | Schneider et al. |
| 9,522,234 | B2 | 12/2016 | Cabiri |
| 9,526,837 | B2 | 12/2016 | Carrel et al. |
| D776,262 | S | 1/2017 | Tyce et al. |
| D776,263 | S | 1/2017 | Tyce et al. |
| D776,264 | S | 1/2017 | Tyce et al. |
| D776,265 | S | 1/2017 | Tyce et al. |
| 9,533,092 | B2 | 1/2017 | Gyrn |
| 9,539,392 | B2 | 1/2017 | Jennings et al. |
| 9,542,826 | B2 | 1/2017 | Edwards et al. |
| 9,555,187 | B2 | 1/2017 | Sonderegger et al. |
| 9,555,191 | B2 | 1/2017 | Edwards et al. |
| 9,572,927 | B2 | 2/2017 | Brüggemann et al. |
| 9,572,932 | B2 | 2/2017 | Eggert et al. |
| 9,579,459 | B2 | 2/2017 | Jennings et al. |
| 9,579,461 | B2 | 2/2017 | Sonderegger et al. |
| 9,586,737 | B2 | 3/2017 | Klumpen |
| 9,597,450 | B2 | 3/2017 | Cindrich et al. |
| 9,597,458 | B2 | 3/2017 | Ashmead et al. |
| 9,598,195 | B2 | 3/2017 | Deutschle et al. |
| 9,604,003 | B2 | 3/2017 | Brereton et al. |
| 9,610,407 | B2 | 4/2017 | Bruggemann et al. |
| 9,623,181 | B2 | 4/2017 | Brereton et al. |
| 9,623,186 | B2 | 4/2017 | Matsutani et al. |
| 9,636,451 | B2 | 5/2017 | Gonnelli et al. |
| 9,636,459 | B2 | 5/2017 | Brereton et al. |
| 9,642,969 | B2 | 5/2017 | Ivosevic et al. |
| 9,656,021 | B2 | 5/2017 | Brereton et al. |
| 9,669,163 | B2 | 6/2017 | McNall, III et al. |
| 9,675,752 | B2 | 6/2017 | Christensen |
| 9,687,607 | B2 | 6/2017 | Brereton et al. |
| D791,306 | S | 7/2017 | Clemente et al. |

(56) References Cited

U.S. PATENT DOCUMENTS

| | | | |
|---|---|---|---|
| 9,707,335 B2 | 7/2017 | Agard et al. |
| 9,707,337 B2 | 7/2017 | O'Connor et al. |
| 9,707,352 B2 | 7/2017 | Helmer et al. |
| D794,770 S | 8/2017 | Wu et al. |
| D794,771 S | 8/2017 | Wu et al. |
| D794,776 S | 8/2017 | Tyce et al. |
| 9,717,850 B2 | 8/2017 | Sonderegger |
| 9,717,858 B2 | 8/2017 | Hara et al. |
| 9,718,881 B2 | 8/2017 | Gromada et al. |
| 9,724,471 B2 | 8/2017 | Edwards et al. |
| 9,731,074 B2 | 8/2017 | Ishikawa et al. |
| 9,737,655 B2 | 8/2017 | Clemente et al. |
| 9,737,669 B2 | 8/2017 | Edwards et al. |
| 9,744,297 B2 | 8/2017 | Cabiri et al. |
| 9,752,003 B2 | 9/2017 | Minagawa |
| 9,764,092 B2 | 9/2017 | Cabiri |
| 9,775,957 B2 | 10/2017 | Despa et al. |
| 9,789,255 B2 | 10/2017 | Brereton et al. |
| 9,795,735 B2 | 10/2017 | Levesque et al. |
| 9,802,030 B2 | 10/2017 | Clemente et al. |
| D804,019 S | 11/2017 | Costello et al. |
| 9,814,832 B2 | 11/2017 | Agard et al. |
| 9,814,838 B2 | 11/2017 | Edwards et al. |
| 9,821,117 B2 | 11/2017 | Anderson et al. |
| 9,821,120 B2 | 11/2017 | Nakano |
| 9,827,377 B2 | 11/2017 | Takai et al. |
| D804,650 S | 12/2017 | Costello et al. |
| D805,186 S | 12/2017 | Costello et al. |
| D805,187 S | 12/2017 | Costello et al. |
| D805,188 S | 12/2017 | Costello et al. |
| D805,189 S | 12/2017 | Costello et al. |
| D805,190 S | 12/2017 | Costello et al. |
| D805,632 S | 12/2017 | Costello et al. |
| D805,633 S | 12/2017 | Costello et al. |
| D806,234 S | 12/2017 | Costello et al. |
| D806,235 S | 12/2017 | Costello et al. |
| 9,833,561 B2 | 12/2017 | Chambers et al. |
| 9,833,562 B2 | 12/2017 | Sonderegger et al. |
| 9,833,573 B2 | 12/2017 | Edwards et al. |
| 9,836,948 B2 | 12/2017 | Edwards et al. |
| 9,850,445 B2 | 12/2017 | Minagawa |
| D806,863 S | 1/2018 | Costello et al. |
| D807,499 S | 1/2018 | Costello et al. |
| D808,011 S | 1/2018 | Costello et al. |
| 9,855,390 B2 | 1/2018 | Bisegna et al. |
| 9,867,938 B2 | 1/2018 | Edwards et al. |
| 9,867,946 B2 | 1/2018 | Iwano et al. |
| 9,872,633 B2 | 1/2018 | Limaye et al. |
| 9,878,091 B2 | 1/2018 | Cabiri |
| D810,278 S | 2/2018 | Cabiri et al. |
| D810,279 S | 2/2018 | Cabiri et al. |
| D811,583 S | 2/2018 | Cabiri et al. |
| D811,584 S | 2/2018 | Cabiri et al. |
| 9,889,254 B2 | 2/2018 | Haenggi |
| D812,738 S | 3/2018 | Wolford |
| D812,739 S | 3/2018 | Wolford |
| D813,380 S | 3/2018 | Stonecipher et al. |
| 9,911,308 B2 | 3/2018 | Edwards et al. |
| 9,913,942 B2 | 3/2018 | Brereton et al. |
| 9,919,097 B2 | 3/2018 | Sonderegger et al. |
| 9,925,342 B2 | 3/2018 | Carrel et al. |
| 9,925,344 B2 | 3/2018 | Brereton et al. |
| 9,943,653 B2 | 4/2018 | Kamen et al. |
| 9,950,123 B2 | 4/2018 | Brereton et al. |
| D817,481 S | 5/2018 | Cabiri et al. |
| 9,956,345 B2 | 5/2018 | Anderson et al. |
| 9,968,731 B2 | 5/2018 | Gonnelli et al. |
| 9,981,083 B2 | 5/2018 | Gonnelli et al. |
| 9,981,088 B2 | 5/2018 | Byerly |
| 9,981,089 B2 | 5/2018 | Ishida et al. |
| 9,987,419 B2 | 6/2018 | Hanson et al. |
| 9,987,428 B2 | 6/2018 | Tan-Malecki et al. |
| 9,999,724 B2 | 6/2018 | Cindrich et al. |
| 9,999,727 B2 | 6/2018 | O'Connor et al. |
| 10,004,832 B2 | 6/2018 | Yotsutsuji |
| 10,023,644 B2 | 7/2018 | Gromada et al. |
| 10,046,115 B2 | 8/2018 | Bokelman et al. |
| 10,058,658 B1 | 8/2018 | Voytilla |
| 10,071,196 B2 | 9/2018 | Cabiri |
| 10,071,198 B2 | 9/2018 | Cabiri et al. |
| 10,071,203 B2 | 9/2018 | Edwards et al. |
| 10,076,605 B2 | 9/2018 | Marbet et al. |
| 10,076,611 B2 | 9/2018 | Edwards et al. |
| 10,080,837 B2 | 9/2018 | Meehan et al. |
| 10,080,846 B2 | 9/2018 | Sonderegger et al. |
| 10,092,693 B2 | 10/2018 | Hanson et al. |
| 10,099,005 B2 | 10/2018 | Gao et al. |
| 10,099,023 B2 | 10/2018 | Edwards et al. |
| 10,105,489 B2 | 10/2018 | Edwards et al. |
| 10,124,112 B2 | 11/2018 | Diianni et al. |
| 10,124,113 B2 | 11/2018 | Tieck et al. |
| 10,130,758 B2 | 11/2018 | Diianni et al. |
| 10,130,763 B2 | 11/2018 | Lauchard et al. |
| 10,137,254 B2 | 11/2018 | Larsen et al. |
| 10,143,792 B2 | 12/2018 | Edwards et al. |
| 10,143,801 B2 | 12/2018 | Schabbach et al. |
| 10,149,947 B2 | 12/2018 | Bayer et al. |
| 10,155,086 B2 | 12/2018 | Sugimoto et al. |
| 10,159,785 B2 | 12/2018 | Cabiri |
| 10,159,799 B2 | 12/2018 | Kondoh et al. |
| D838,840 S | 1/2019 | Cabiri et al. |
| D839,413 S | 1/2019 | Wohlfahrt et al. |
| D839,416 S | 1/2019 | Wohlfahrt et al. |
| 10,166,336 B2 | 1/2019 | Lumme et al. |
| 10,173,001 B2 | 1/2019 | Schabbach et al. |
| 10,173,013 B2 | 1/2019 | Kaneko et al. |
| 10,179,204 B2 | 1/2019 | Cabiri |
| 10,182,969 B2 | 1/2019 | Arnott et al. |
| 10,183,116 B2 | 1/2019 | Edwards et al. |
| 10,183,117 B2 | 1/2019 | Fraunhofer et al. |
| D840,531 S | 2/2019 | Guillermo |
| 10,293,965 B2 | 5/2019 | Lu et al. |
| 10,314,968 B2 | 6/2019 | Bruggemann et al. |
| 10,358,495 B2 | 7/2019 | Ullman et al. |
| 10,391,245 B2 | 8/2019 | Cronenberg et al. |
| 10,413,667 B2 | 9/2019 | Henderson et al. |
| 10,426,892 B2 | 10/2019 | Stefanov |
| 10,518,041 B2 | 12/2019 | Brereton et al. |
| 10,525,193 B2 | 1/2020 | Schauderna |
| 10,532,155 B2 | 1/2020 | Schiendzielorz |
| D876,618 S | 2/2020 | Nazzaro et al. |
| 10,549,029 B2 | 2/2020 | Agard et al. |
| 10,549,044 B2 | 2/2020 | Quinn et al. |
| 10,556,064 B2 | 2/2020 | Brereton et al. |
| D877,893 S | 3/2020 | Stonecipher et al. |
| D878,555 S | 3/2020 | Farris et al. |
| D878,556 S | 3/2020 | Farris et al. |
| D878,557 S | 3/2020 | Farris et al. |
| D878,559 S | 3/2020 | Stonecipher et al. |
| 10,583,241 B2 | 3/2020 | Wu et al. |
| 10,583,245 B2 | 3/2020 | McCullough et al. |
| 10,603,445 B2 | 3/2020 | Quinn et al. |
| D882,760 S | 4/2020 | Katz et al. |
| D882,761 S | 4/2020 | Cabiri et al. |
| D882,765 S | 4/2020 | Farris et al. |
| 10,610,640 B2 | 4/2020 | Gonnelli et al. |
| 10,617,819 B2 | 4/2020 | Cabiri et al. |
| 10,632,249 B2 | 4/2020 | Marbet et al. |
| 10,632,253 B2 | 4/2020 | Uchiyama et al. |
| 10,646,643 B2 | 5/2020 | Cabiri et al. |
| 10,661,015 B2 | 5/2020 | Rioux et al. |
| D887,893 S | 6/2020 | Beauregard et al. |
| 10,668,227 B2 | 6/2020 | Caspers |
| 10,682,458 B2 | 6/2020 | Wu et al. |
| 10,695,485 B2 | 6/2020 | Nazzaro |
| 10,695,487 B2 | 6/2020 | Hanson et al. |
| 10,722,646 B2 | 7/2020 | Cole et al. |
| 10,726,701 B2 | 7/2020 | Edwards et al. |
| D894,373 S | 8/2020 | Haug et al. |
| 10,737,019 B2 | 8/2020 | Henderson et al. |
| 10,751,476 B2 | 8/2020 | Gazeley et al. |
| 10,758,683 B2 | 9/2020 | Gibson et al. |
| 10,765,801 B2 | 9/2020 | McCullough |
| 10,765,807 B2 | 9/2020 | Allis et al. |

(56)                  References Cited

U.S. PATENT DOCUMENTS

| | | | |
|---|---|---|---|
| 10,773,024 B2 | 9/2020 | Cronenberg et al. | |
| 10,780,227 B2 | 9/2020 | Young | |
| 10,792,424 B2 | 10/2020 | Sasaki | |
| 10,792,425 B2 | 10/2020 | Joseph et al. | |
| 10,792,432 B2 | 10/2020 | Gazeley et al. | |
| 10,793,624 B2 | 10/2020 | Orengo et al. | |
| 10,799,630 B2 | 10/2020 | McCullough | |
| 10,799,631 B2 | 10/2020 | Barmaimon et al. | |
| 10,799,644 B2 | 10/2020 | Hansen et al. | |
| 10,806,854 B2 | 10/2020 | O'Connor et al. | |
| 10,806,855 B2 | 10/2020 | Destefano et al. | |
| 10,828,430 B2 | 11/2020 | Kondo | |
| 10,842,947 B2 | 11/2020 | Helmer | |
| 10,850,028 B2 | 12/2020 | Caspers | |
| 10,874,792 B2 | 12/2020 | Meehan et al. | |
| 10,894,128 B2 | 1/2021 | Bokelman et al. | |
| 10,898,656 B2 | 1/2021 | McCaffrey et al. | |
| 10,912,887 B2 | 2/2021 | Ishikawa et al. | |
| 10,918,788 B2 | 2/2021 | O'Connor et al. | |
| 10,918,791 B2 | 2/2021 | Edwards et al. | |
| 10,926,023 B2 | 2/2021 | Falkovich | |
| D914,200 S | 3/2021 | Gregory et al. | |
| 10,933,188 B2 | 3/2021 | Gonnelli et al. | |
| 10,933,189 B2 | 3/2021 | Bente, IV et al. | |
| 10,933,192 B2 | 3/2021 | Hanson et al. | |
| 10,946,136 B2 | 3/2021 | Prudden et al. | |
| 10,953,157 B2 | 3/2021 | Klemm et al. | |
| 10,960,134 B2 | 3/2021 | Salter et al. | |
| 10,967,118 B2 | 4/2021 | Barmaimon et al. | |
| 10,967,127 B2 | 4/2021 | Murakami et al. | |
| 10,980,938 B2 | 4/2021 | Barmaimon et al. | |
| 10,980,939 B2 | 4/2021 | Kondo et al. | |
| 10,987,466 B2 | 4/2021 | Johnson et al. | |
| 10,987,467 B2 | 4/2021 | Cole et al. | |
| 11,000,651 B2 | 5/2021 | Anderson et al. | |
| 11,033,676 B2 | 6/2021 | Dechelette et al. | |
| 11,033,679 B2 | 6/2021 | Hanson et al. | |
| 11,033,688 B2 | 6/2021 | Helmer et al. | |
| 11,040,135 B2 | 6/2021 | Clemente et al. | |
| 11,040,137 B2 | 6/2021 | Wei | |
| 11,045,603 B2 | 6/2021 | McCaffrey et al. | |
| 11,058,605 B2 | 7/2021 | Barmaimon et al. | |
| 11,058,817 B2 | 7/2021 | Sugimoto et al. | |
| 11,077,246 B2 | 8/2021 | Nekouzadeh et al. | |
| 11,103,636 B2 | 8/2021 | Olivas et al. | |
| 11,103,680 B2 | 8/2021 | Cole | |
| 11,110,225 B2 | 9/2021 | Tan-Malecki et al. | |
| 11,129,936 B2 | 9/2021 | Gibson et al. | |
| 11,129,941 B2 | 9/2021 | Tan-Malecki et al. | |
| 11,129,943 B2 | 9/2021 | Nazzaro et al. | |
| 11,154,654 B2 | 10/2021 | Hirschel et al. | |
| 11,160,931 B2 | 11/2021 | Tan-Malecki et al. | |
| 11,167,082 B2 | 11/2021 | Laurence et al. | |
| 11,173,244 B2 | 11/2021 | Agard et al. | |
| 11,185,629 B2 | 11/2021 | Weibel et al. | |
| D938,578 S | 12/2021 | Kolenda et al. | |
| 11,197,954 B2 | 12/2021 | Staub et al. | |
| 11,202,858 B2 | 12/2021 | Yigal et al. | |
| 11,213,624 B2 | 1/2022 | McCullough et al. | |
| 11,213,626 B2 | 1/2022 | Paramanandam et al. | |
| 11,229,738 B2 | 1/2022 | Møller | |
| 11,229,741 B2 | 1/2022 | Diianni et al. | |
| 11,241,527 B2 | 2/2022 | Rabolli | |
| 11,241,529 B2 | 2/2022 | Pizzochero et al. | |
| 11,241,531 B2 | 2/2022 | Sasaki | |
| 11,253,652 B2 | 2/2022 | Egloff et al. | |
| 11,260,170 B2 | 3/2022 | Schabbach et al. | |
| 11,260,171 B2 | 3/2022 | Smith | |
| 11,260,172 B2 | 3/2022 | Barmaimon et al. | |
| 11,263,921 B2 | 3/2022 | Edwards et al. | |
| 11,266,777 B2 | 3/2022 | Gibson et al. | |
| 11,266,787 B2 | 3/2022 | Dahmani et al. | |
| 11,273,260 B2 | 3/2022 | Tan-Malecki et al. | |
| 11,278,666 B2 | 3/2022 | Wei | |
| 11,285,260 B2 | 3/2022 | Cole | |
| 11,285,266 B2 | 3/2022 | Fitzgibbon et al. | |
| 11,291,774 B2 | 4/2022 | Bayer et al. | |
| 11,298,463 B2 | 4/2022 | Tan-Malecki et al. | |
| 11,311,666 B1 | 4/2022 | West et al. | |
| 11,311,670 B2 | 4/2022 | Barmaimon et al. | |
| D950,713 S | 5/2022 | Bin et al. | |
| D950,714 S | 5/2022 | Jeon et al. | |
| D951,434 S | 5/2022 | Boyaval et al. | |
| D955,564 S | 6/2022 | Boyaval et al. | |
| D956,217 S | 6/2022 | Jeon et al. | |
| 11,357,916 B2 | 6/2022 | McCullough et al. | |
| 11,357,918 B2 | 6/2022 | Avery et al. | |
| 11,364,337 B2 | 6/2022 | Cabiri et al. | |
| 11,364,341 B2 | 6/2022 | Rioux et al. | |
| 11,364,344 B2 | 6/2022 | Rabolli | |
| 11,369,736 B2 | 6/2022 | Coiner et al. | |
| 11,383,026 B2 | 7/2022 | Russo | |
| 11,383,038 B2 | 7/2022 | Nazzaro et al. | |
| 11,383,047 B2 | 7/2022 | Gibson et al. | |
| 11,389,598 B2 | 7/2022 | Yigal et al. | |
| 11,400,215 B2 | 8/2022 | Cowe et al. | |
| 11,400,226 B2 | 8/2022 | Yigal et al. | |
| 11,406,565 B2 | 8/2022 | Arnott et al. | |
| 11,413,393 B2 | 8/2022 | Bourelle et al. | |
| 11,426,520 B2 | 8/2022 | Edwards et al. | |
| 11,439,748 B2 | 9/2022 | Giambattista et al. | |
| 11,439,759 B2 | 9/2022 | Verlaak et al. | |
| 11,439,767 B2 | 9/2022 | Booth et al. | |
| 11,452,473 B2 | 9/2022 | Zhang et al. | |
| D967,397 S | 10/2022 | Chen | |
| 11,458,281 B2 | 10/2022 | Horvath et al. | |
| 11,471,593 B2 | 10/2022 | Barmaimon et al. | |
| 11,484,644 B2 | 11/2022 | O'Connor et al. | |
| 11,484,656 B2 | 11/2022 | Hagino | |
| 11,490,831 B2 | 11/2022 | Limaye et al. | |
| 11,517,663 B2 | 12/2022 | McCullough et al. | |
| 11,517,664 B2 | 12/2022 | Barmaimon et al. | |
| 11,517,674 B2 | 12/2022 | Edwards et al. | |
| 11,524,112 B2 | 12/2022 | Day et al. | |
| 11,541,167 B2 | 1/2023 | Richards et al. | |
| 11,541,183 B2 | 1/2023 | Hering et al. | |
| 11,547,801 B2 | 1/2023 | Grygus et al. | |
| 11,554,213 B2 | 1/2023 | Stefanov et al. | |
| 11,590,277 B2 | 2/2023 | Stonecipher et al. | |
| 11,590,279 B2 | 2/2023 | Barmaimon et al. | |
| 11,590,286 B2 | 2/2023 | Edwards et al. | |
| 11,590,292 B2 | 2/2023 | Mayle, Jr. et al. | |
| 11,596,733 B2 | 3/2023 | Yodfat et al. | |
| 11,607,505 B1 | 3/2023 | West | |
| D982,742 S | 4/2023 | Cerqueira et al. | |
| 11,617,833 B2 | 4/2023 | Rioux et al. | |
| 11,617,837 B2 | 4/2023 | Olivas et al. | |
| D986,288 S | 5/2023 | Zhang | |
| 11,642,470 B2 | 5/2023 | Bar-El et al. | |
| 11,648,345 B2 | 5/2023 | Nemoto et al. | |
| 11,684,712 B2 | 6/2023 | Smith et al. | |
| 11,766,519 B2 | 9/2023 | Dutta Ray et al. | |
| 11,813,428 B2 | 11/2023 | Barraud et al. | |
| 11,819,663 B2 | 11/2023 | Marcoz et al. | |
| D1,007,676 S | 12/2023 | Grygus | |
| 11,857,757 B2 | 1/2024 | Fridez et al. | |
| 11,883,633 B2 | 1/2024 | Slate et al. | |
| D1,015,529 S | 2/2024 | Cannamela | |
| D1,015,530 S | 2/2024 | Cannamela | |
| D1,029,241 S | 5/2024 | Fett | |
| 11,992,662 B2 | 5/2024 | Dahmani et al. | |
| D1,050,421 S | 11/2024 | Borghi | |
| 2001/0025168 A1 | 9/2001 | Gross et al. | |
| 2002/0043951 A1 | 4/2002 | Moberg | |
| 2002/0046962 A1* | 4/2002 | Vallans | A61B 50/362 |
| | | | 206/370 |
| 2002/0123719 A1 | 9/2002 | Lavi et al. | |
| 2002/0161332 A1 | 10/2002 | Ramey | |
| 2003/0009133 A1 | 1/2003 | Ramey | |
| 2003/0055395 A1 | 3/2003 | Manera | |
| 2003/0083686 A1 | 5/2003 | Freeman et al. | |
| 2003/0097092 A1 | 5/2003 | Flaherty | |
| 2003/0105430 A1 | 6/2003 | Lavi et al. | |
| 2003/0138347 A1 | 7/2003 | Lin | |

(56) References Cited

U.S. PATENT DOCUMENTS

| | | |
|---|---|---|
| 2004/0015134 A1 | 1/2004 | Lavi et al. |
| 2004/0020558 A1 | 2/2004 | Stewart et al. |
| 2004/0030285 A1 | 2/2004 | Lavi et al. |
| 2004/0068176 A1 | 4/2004 | Kuth |
| 2004/0069044 A1 | 4/2004 | Lavi et al. |
| 2004/0092873 A1 | 5/2004 | Moberg |
| 2005/0065472 A1 | 3/2005 | Cindrich et al. |
| 2005/0165363 A1 | 7/2005 | Judson et al. |
| 2005/0197650 A1 | 9/2005 | Sugimoto et al. |
| 2005/0212222 A1 | 9/2005 | Tachikawa et al. |
| 2006/0102178 A1 | 5/2006 | Feiner et al. |
| 2006/0200073 A1 | 9/2006 | Radmer et al. |
| 2006/0282040 A1 | 12/2006 | Toman et al. |
| 2007/0021715 A1 | 1/2007 | Kohlbrenner et al. |
| 2007/0021733 A1 | 1/2007 | Hansen et al. |
| 2007/0088291 A1 | 4/2007 | Weilbacher |
| 2007/0112326 A1 | 5/2007 | Bosshard et al. |
| 2007/0135767 A1 | 6/2007 | Gillespie, III et al. |
| 2007/0178776 A1 | 8/2007 | Etter et al. |
| 2007/0233001 A1 | 10/2007 | Burroughs et al. |
| 2007/0299402 A1 | 12/2007 | Ishii et al. |
| 2008/0051711 A1 | 2/2008 | Mounce et al. |
| 2008/0132843 A1 | 6/2008 | Sharifi |
| 2008/0172988 A1 | 7/2008 | Hwang |
| 2008/0221523 A1 | 9/2008 | Moberg et al. |
| 2008/0234628 A1 | 9/2008 | Dent et al. |
| 2008/0269687 A1 | 10/2008 | Chong et al. |
| 2008/0281297 A1 | 11/2008 | Pesach et al. |
| 2009/0039721 A1 | 2/2009 | Takagi et al. |
| 2009/0048563 A1 | 2/2009 | Ethelfeld et al. |
| 2009/0076383 A1 | 3/2009 | Toews et al. |
| 2009/0093793 A1 | 4/2009 | Gross et al. |
| 2009/0143741 A1 | 6/2009 | Burn |
| 2009/0163860 A1 | 6/2009 | Patrick et al. |
| 2009/0163874 A1 | 6/2009 | Krag et al. |
| 2009/0184596 A1 | 7/2009 | Masato |
| 2009/0236253 A1 | 9/2009 | Merckle et al. |
| 2009/0247982 A1 | 10/2009 | Krulevitch et al. |
| 2009/0254046 A1 | 10/2009 | Hetherington |
| 2009/0288977 A1 | 11/2009 | Vanderbush et al. |
| 2010/0036319 A1 | 2/2010 | Drake et al. |
| 2010/0049125 A1 | 2/2010 | James et al. |
| 2010/0049128 A1 | 2/2010 | Mckenzie et al. |
| 2010/0152674 A1 | 6/2010 | Kavazov et al. |
| 2010/0198187 A1 | 8/2010 | Yodfat et al. |
| 2010/0274200 A1 | 10/2010 | Nielsen |
| 2011/0009814 A1 | 1/2011 | Tsoukalis |
| 2011/0021993 A1 | 1/2011 | Bar-Haim et al. |
| 2011/0054285 A1 | 3/2011 | Searle et al. |
| 2011/0105872 A1 | 5/2011 | Chickering, III et al. |
| 2011/0137255 A1 | 6/2011 | Nielsen et al. |
| 2011/0137257 A1 | 6/2011 | Gyrn et al. |
| 2011/0152779 A1 | 6/2011 | Panotopoulos |
| 2011/0224616 A1 | 9/2011 | Slate et al. |
| 2011/0270220 A1 | 11/2011 | Genosar |
| 2012/0022499 A1 | 1/2012 | Anderson et al. |
| 2012/0035546 A1 | 2/2012 | Cabiri |
| 2012/0051967 A1 | 3/2012 | Murphy et al. |
| 2012/0071829 A1 | 3/2012 | Edwards et al. |
| 2012/0071837 A1 | 3/2012 | O'Connor et al. |
| 2012/0095409 A1 | 4/2012 | Lanin et al. |
| 2012/0116212 A1 | 5/2012 | Bral |
| 2012/0123387 A1 | 5/2012 | Gonzalez et al. |
| 2012/0130318 A1 | 5/2012 | Young |
| 2012/0211946 A1 | 8/2012 | Halili et al. |
| 2012/0238962 A1 | 9/2012 | Chin et al. |
| 2012/0252709 A1 | 10/2012 | Felts et al. |
| 2012/0253314 A1 | 10/2012 | Harish et al. |
| 2012/0265127 A1 | 10/2012 | Buri et al. |
| 2012/0310173 A1 | 12/2012 | Sonderegger |
| 2012/0310175 A1 | 12/2012 | Vedrine et al. |
| 2012/0323183 A1 | 12/2012 | Peterson et al. |
| 2012/0330235 A1 | 12/2012 | Moga et al. |
| 2013/0006195 A1 | 1/2013 | Sonderegger et al. |
| 2013/0008137 A1 | 1/2013 | Py |
| 2013/0012872 A1 | 1/2013 | Gross et al. |
| 2013/0012874 A1 | 1/2013 | Gross et al. |
| 2013/0012875 A1 | 1/2013 | Gross et al. |
| 2013/0053786 A1 | 2/2013 | Maeda et al. |
| 2013/0066274 A1 | 3/2013 | O'Connor et al. |
| 2013/0079747 A1 | 3/2013 | Gross et al. |
| 2013/0090605 A1 | 4/2013 | O'Connor et al. |
| 2013/0172819 A1 | 7/2013 | Iio et al. |
| 2013/0178826 A1 | 7/2013 | Li |
| 2013/0180618 A1 | 7/2013 | Py |
| 2013/0204224 A1 | 8/2013 | Müller-Pathle et al. |
| 2013/0211344 A1 | 8/2013 | Rodriguez et al. |
| 2013/0211374 A1 | 8/2013 | Hetherington |
| 2013/0218089 A1 | 8/2013 | Davies et al. |
| 2013/0218092 A1 | 8/2013 | Davies et al. |
| 2013/0237916 A1 | 9/2013 | Hanson et al. |
| 2013/0245604 A1 | 9/2013 | Kouyoumjian et al. |
| 2013/0281932 A1 | 10/2013 | Harish et al. |
| 2013/0310757 A1 | 11/2013 | Brereton et al. |
| 2013/0316110 A1 | 11/2013 | Sudo |
| 2013/0317427 A1 | 11/2013 | Brereton et al. |
| 2013/0317430 A1 | 11/2013 | Brereton et al. |
| 2013/0338584 A1 | 12/2013 | Mounce et al. |
| 2013/0345626 A1 | 12/2013 | Tennican |
| 2014/0005596 A1 | 1/2014 | Schuster |
| 2014/0008366 A1 | 1/2014 | Genosar |
| 2014/0013718 A1* | 1/2014 | Maasarani ......... B65D 77/2032 |
| | | 206/364 |
| 2014/0039405 A1 | 2/2014 | Konandreas et al. |
| 2014/0052055 A1 | 2/2014 | Yodfat et al. |
| 2014/0058349 A1 | 2/2014 | Bazargan et al. |
| 2014/0074062 A1 | 3/2014 | Caffey et al. |
| 2014/0083517 A1 | 3/2014 | Moia et al. |
| 2014/0088508 A1 | 3/2014 | Ryan et al. |
| 2014/0088553 A1 | 3/2014 | Hetherington |
| 2014/0128815 A1 | 5/2014 | Cabiri et al. |
| 2014/0128840 A1 | 5/2014 | Rao et al. |
| 2014/0142507 A1 | 5/2014 | Armes |
| 2014/0148760 A1 | 5/2014 | Ishikawa et al. |
| 2014/0148784 A1 | 5/2014 | Anderson et al. |
| 2014/0171871 A1 | 6/2014 | Mathews et al. |
| 2014/0171872 A1 | 6/2014 | Mathews et al. |
| 2014/0200510 A1 | 7/2014 | Agard et al. |
| 2014/0207075 A1 | 7/2014 | Yotsutsuji |
| 2014/0213975 A1 | 7/2014 | Clemente et al. |
| 2014/0214000 A1 | 7/2014 | Moia et al. |
| 2014/0221930 A1 | 8/2014 | Kuster et al. |
| 2014/0224688 A1* | 8/2014 | Slemmen ............ A61M 5/3204 |
| | | 206/365 |
| 2014/0236086 A1 | 8/2014 | Levesque et al. |
| 2014/0236096 A1 | 8/2014 | Helmer et al. |
| 2014/0238542 A1 | 8/2014 | Kvale |
| 2014/0243749 A1 | 8/2014 | Edwards et al. |
| 2014/0288511 A1 | 9/2014 | Tan-Malecki et al. |
| 2014/0296787 A1 | 10/2014 | Agard et al. |
| 2014/0296824 A1 | 10/2014 | Edwards et al. |
| 2014/0316376 A1 | 10/2014 | Wall |
| 2014/0319778 A1 | 10/2014 | Kawasaki et al. |
| 2014/0336578 A1 | 11/2014 | Brereton et al. |
| 2014/0339777 A1 | 11/2014 | Nakano et al. |
| 2015/0011973 A1 | 1/2015 | Edwards et al. |
| 2015/0057613 A1 | 2/2015 | Clemente et al. |
| 2015/0080800 A1 | 3/2015 | Cronenberg |
| 2015/0088077 A1 | 3/2015 | Kemp et al. |
| 2015/0088092 A1 | 3/2015 | Holm et al. |
| 2015/0119674 A1 | 4/2015 | Fischell et al. |
| 2015/0126926 A1 | 5/2015 | Giambattista et al. |
| 2015/0144793 A1 | 5/2015 | Whalley et al. |
| 2015/0148751 A1 | 5/2015 | Yotsutsuji |
| 2015/0157786 A1 | 6/2015 | Sonderegger et al. |
| 2015/0157804 A1 | 6/2015 | Baba et al. |
| 2015/0174323 A1 | 6/2015 | Edwards et al. |
| 2015/0174326 A1 | 6/2015 | Bokelman et al. |
| 2015/0182686 A1* | 7/2015 | Okihara ............. B65D 79/0084 |
| | | 206/365 |
| 2015/0190588 A1 | 7/2015 | Hanson et al. |
| 2015/0202367 A1 | 7/2015 | Plaschkes et al. |
| 2015/0203612 A1 | 7/2015 | Minagawa |
| 2015/0209505 A1 | 7/2015 | Hanson et al. |

(56) References Cited

U.S. PATENT DOCUMENTS

| | | |
|---|---|---|
| 2015/0209519 A1 | 7/2015 | Mernøe |
| 2015/0217045 A1 | 8/2015 | Bente, IV et al. |
| 2015/0231336 A1 | 8/2015 | Edwards et al. |
| 2015/0265767 A1 | 9/2015 | Vazquez et al. |
| 2015/0265768 A1 | 9/2015 | Vazquez et al. |
| 2015/0273151 A1 | 10/2015 | McLoughlin et al. |
| 2015/0273155 A1 | 10/2015 | Kaneko et al. |
| 2015/0290392 A1 | 10/2015 | Henderson et al. |
| 2015/0290394 A1 | 10/2015 | Murakami et al. |
| 2015/0297827 A1 | 10/2015 | Hanson et al. |
| 2015/0306306 A1 | 10/2015 | Gonnelli et al. |
| 2015/0306307 A1 | 10/2015 | Cole et al. |
| 2015/0359965 A1 | 12/2015 | O'Connor et al. |
| 2015/0374912 A1 | 12/2015 | Sugimoto et al. |
| 2016/0008542 A1 | 1/2016 | Hirschel et al. |
| 2016/0015907 A1 | 1/2016 | Edwards et al. |
| 2016/0022909 A1 | 1/2016 | Edwards et al. |
| 2016/0022918 A1 | 1/2016 | Gunzel |
| 2016/0030665 A1 | 2/2016 | Cabiri |
| 2016/0045670 A1 | 2/2016 | Edwards et al. |
| 2016/0045673 A1 | 2/2016 | Bayer et al. |
| 2016/0058941 A1 | 3/2016 | Wu et al. |
| 2016/0058945 A1 | 3/2016 | Piscitelli |
| 2016/0058949 A1 | 3/2016 | Bayer et al. |
| 2016/0067417 A1 | 3/2016 | Bayer et al. |
| 2016/0082182 A1 | 3/2016 | Gregory et al. |
| 2016/0082189 A1 | 3/2016 | Anderson et al. |
| 2016/0082193 A1 | 3/2016 | Laubach et al. |
| 2016/0089056 A1 | 3/2016 | Limaye et al. |
| 2016/0101239 A1 | 4/2016 | Ishida et al. |
| 2016/0106912 A1 | 4/2016 | Gross et al. |
| 2016/0106923 A1 | 4/2016 | Brereton et al. |
| 2016/0121056 A1 | 5/2016 | Edwards et al. |
| 2016/0129194 A1 | 5/2016 | Brereton et al. |
| 2016/0129202 A1 | 5/2016 | Carrel et al. |
| 2016/0158435 A1 | 6/2016 | Wu et al. |
| 2016/0158463 A1 | 6/2016 | Kamen et al. |
| 2016/0175515 A1 | 6/2016 | McCullough |
| 2016/0175527 A1 | 6/2016 | McCullough |
| 2016/0184514 A1 | 6/2016 | Kamen et al. |
| 2016/0184521 A1 | 6/2016 | Edwards et al. |
| 2016/0184535 A1 | 6/2016 | Edwards et al. |
| 2016/0193405 A1 | 7/2016 | Schabbach et al. |
| 2016/0213837 A1 | 7/2016 | Schabbach et al. |
| 2016/0213838 A1 | 7/2016 | Schabbach et al. |
| 2016/0213840 A1 | 7/2016 | Schabbach et al. |
| 2016/0228644 A1 | 8/2016 | Cabiri |
| 2016/0235916 A1 | 8/2016 | Edwards et al. |
| 2016/0243308 A1 | 8/2016 | Giraud et al. |
| 2016/0243311 A1 | 8/2016 | Fournier et al. |
| 2016/0243318 A1 | 8/2016 | Despa et al. |
| 2016/0250414 A1 | 9/2016 | Edwards et al. |
| 2016/0262984 A1 | 9/2016 | Arnott et al. |
| 2016/0263324 A1 | 9/2016 | Shaanan et al. |
| 2016/0271323 A1 | 9/2016 | Brüggemann et al. |
| 2016/0279330 A1 | 9/2016 | Schabbach et al. |
| 2016/0287800 A1 | 10/2016 | Nakano et al. |
| 2016/0317736 A1 | 11/2016 | Schabbach et al. |
| 2016/0317737 A1 | 11/2016 | Schabbach et al. |
| 2016/0325044 A1 | 11/2016 | Tschirren et al. |
| 2016/0354553 A1 | 12/2016 | Anderson et al. |
| 2016/0367752 A1 | 12/2016 | Cindrich et al. |
| 2017/0014576 A1 | 1/2017 | Abe et al. |
| 2017/0020557 A1 | 1/2017 | Onuma |
| 2017/0021096 A1 | 1/2017 | Cole et al. |
| 2017/0021103 A1 | 1/2017 | Mosebach et al. |
| 2017/0021107 A1 | 1/2017 | Kaneko et al. |
| 2017/0021108 A1 | 1/2017 | Swal et al. |
| 2017/0021137 A1 | 1/2017 | Cole |
| 2017/0028132 A1 | 2/2017 | Cronenberg et al. |
| 2017/0035957 A1 | 2/2017 | Edwards et al. |
| 2017/0035961 A1 | 2/2017 | Cabiri |
| 2017/0037212 A1 | 2/2017 | Minagawa |
| 2017/0043101 A1 | 2/2017 | Cole et al. |
| 2017/0049954 A1 | 2/2017 | Edwards et al. |
| 2017/0049958 A1 | 2/2017 | Cronenberg et al. |
| 2017/0049965 A1 | 2/2017 | Baker et al. |
| 2017/0056582 A1 | 3/2017 | Niklaus |
| 2017/0080149 A1 | 3/2017 | O'Connor et al. |
| 2017/0092101 A1 | 3/2017 | Edwards et al. |
| 2017/0095614 A1 | 4/2017 | Sonderegger et al. |
| 2017/0098058 A1 | 4/2017 | McCullough et al. |
| 2017/0103186 A1 | 4/2017 | McCullough et al. |
| 2017/0119959 A1 | 5/2017 | Cole et al. |
| 2017/0119969 A1 | 5/2017 | McCullough et al. |
| 2017/0124284 A1 | 5/2017 | McCullough et al. |
| 2017/0124285 A1 | 5/2017 | McCullough et al. |
| 2017/0128665 A1 | 5/2017 | Mathews et al. |
| 2017/0143908 A1 | 5/2017 | Eggert et al. |
| 2017/0165418 A1 | 6/2017 | Bainton et al. |
| 2017/0173266 A1 | 6/2017 | Ashmead et al. |
| 2017/0173267 A1 | 6/2017 | Ashmead et al. |
| 2017/0182242 A1 | 6/2017 | Galitz et al. |
| 2017/0182243 A1 | 6/2017 | Cole et al. |
| 2017/0189609 A1 | 7/2017 | Wei |
| 2017/0189610 A1 | 7/2017 | Gonnelli et al. |
| 2017/0197029 A1 | 7/2017 | Cindrich et al. |
| 2017/0197036 A1 | 7/2017 | Brereton et al. |
| 2017/0203033 A1 | 7/2017 | Horvath et al. |
| 2017/0203043 A1 | 7/2017 | Rusch et al. |
| 2017/0203046 A1 | 7/2017 | Larose |
| 2017/0209648 A1 | 7/2017 | Butts et al. |
| 2017/0216526 A1 | 8/2017 | Brereton et al. |
| 2017/0224915 A1 | 8/2017 | Destefano et al. |
| 2017/0232202 A1 | 8/2017 | Yotsutsuji |
| 2017/0239414 A1 | 8/2017 | Barmaimon et al. |
| 2017/0246384 A1 | 8/2017 | Pizzochero et al. |
| 2017/0246397 A1 | 8/2017 | Brereton et al. |
| 2017/0246398 A1 | 8/2017 | Brereton et al. |
| 2017/0252508 A1 | 9/2017 | Schiendzielorz |
| 2017/0252509 A1 | 9/2017 | Caspers |
| 2017/0252510 A1 | 9/2017 | Sonderegger et al. |
| 2017/0258987 A1 | 9/2017 | Caspers |
| 2017/0258994 A1 | 9/2017 | Schiendzielorz |
| 2017/0259014 A1 | 9/2017 | Nessel |
| 2017/0259015 A1 | 9/2017 | Caspers |
| 2017/0266386 A1 | 9/2017 | Kaneko |
| 2017/0266390 A1 | 9/2017 | Baba et al. |
| 2017/0281854 A1 | 10/2017 | Mathews et al. |
| 2017/0281859 A1 | 10/2017 | Agard et al. |
| 2017/0290975 A1 | 10/2017 | Barmaimon et al. |
| 2017/0290977 A1 | 10/2017 | Schauderna |
| 2017/0290981 A1 | 10/2017 | Hoeholt et al. |
| 2017/0290982 A1 | 10/2017 | Edwards et al. |
| 2017/0296741 A1 | 10/2017 | Gregory |
| 2017/0296752 A1 | 10/2017 | Masuyama et al. |
| 2017/0296756 A1 | 10/2017 | Giraud et al. |
| 2017/0304539 A1 | 10/2017 | Ishikawa et al. |
| 2017/0312433 A1 | 11/2017 | Edwards et al. |
| 2017/0319790 A1 | 11/2017 | Andersen et al. |
| 2017/0340827 A1 | 11/2017 | Nazzaro et al. |
| 2017/0340837 A1 | 11/2017 | Nazzaro et al. |
| 2017/0348479 A1 | 12/2017 | Choate et al. |
| 2017/0354781 A1 | 12/2017 | Cronenberg et al. |
| 2017/0354782 A1 | 12/2017 | Quinn et al. |
| 2017/0354783 A1 | 12/2017 | Gazeley et al. |
| 2017/0354785 A1 | 12/2017 | Gazeley et al. |
| 2017/0354788 A1 | 12/2017 | Quinn et al. |
| 2017/0361015 A1 | 12/2017 | McCullough |
| 2017/0361016 A1 | 12/2017 | Levesque et al. |
| 2017/0368260 A1 | 12/2017 | McCullough et al. |
| 2017/0368264 A1 | 12/2017 | Fournier et al. |
| 2017/0368269 A1 | 12/2017 | Kondo |
| 2018/0008769 A1 | 1/2018 | O'Connor et al. |
| 2018/0008774 A1 | 1/2018 | Edwards et al. |
| 2018/0015222 A1 | 1/2018 | Sasaki |
| 2018/0021508 A1 | 1/2018 | Destefano et al. |
| 2018/0028747 A1 | 2/2018 | Hanson et al. |
| 2018/0033286 A1 | 2/2018 | Edwards et al. |
| 2018/0036489 A1 | 2/2018 | Nakano et al. |
| 2018/0036490 A1 | 2/2018 | Minagawa |
| 2018/0043091 A1 | 2/2018 | Agard et al. |
| 2018/0043102 A1 | 2/2018 | Cojocariu et al. |
| 2018/0055995 A1 | 3/2018 | Hanson et al. |

(56) References Cited

U.S. PATENT DOCUMENTS

| | | |
|---|---|---|
| 2018/0056009 A1 | 3/2018 | Filman et al. |
| 2018/0079119 A1 | 3/2018 | Morris et al. |
| 2018/0085517 A1 | 3/2018 | Laurence et al. |
| 2018/0085521 A1 | 3/2018 | Allis et al. |
| 2018/0102066 A1 | 4/2018 | Edwards et al. |
| 2018/0103870 A1 | 4/2018 | Limaye et al. |
| 2018/0117251 A1 | 5/2018 | Rioux et al. |
| 2018/0126082 A1 | 5/2018 | Edwards et al. |
| 2018/0154079 A1 | 6/2018 | Anderson et al. |
| 2018/0177951 A1 | 6/2018 | Sakashita |
| 2018/0185571 A1 | 7/2018 | Clemente et al. |
| 2018/0185579 A1 | 7/2018 | Joseph et al. |
| 2018/0193557 A1 | 7/2018 | Johnson et al. |
| 2018/0200425 A1 | 7/2018 | Kondo et al. |
| 2018/0200445 A1 | 7/2018 | Brereton et al. |
| 2018/0207308 A1 | 7/2018 | Okihara |
| 2018/0207358 A1 | 7/2018 | Uchiyama et al. |
| 2018/0214631 A1 | 8/2018 | Amirouche |
| 2018/0221569 A1 | 8/2018 | Gonnelli et al. |
| 2018/0221573 A1 | 8/2018 | Hanson et al. |
| 2018/0228966 A1 | 8/2018 | Barmaimon et al. |
| 2018/0236173 A1 | 8/2018 | Mccaffrey et al. |
| 2018/0243503 A1 | 8/2018 | Gonnelli et al. |
| 2018/0250472 A1 | 9/2018 | Anderson et al. |
| 2018/0256815 A1 | 9/2018 | Nazzaro |
| 2018/0256823 A1 | 9/2018 | Nazzaro et al. |
| 2018/0264193 A1 | 9/2018 | O'Connor et al. |
| 2018/0266565 A1 | 9/2018 | Minagawa |
| 2018/0272058 A1 | 9/2018 | Pizzochero et al. |
| 2018/0272059 A1 | 9/2018 | Marbet et al. |
| 2018/0272072 A1 | 9/2018 | Radmer et al. |
| 2018/0280607 A1 | 10/2018 | Richards et al. |
| 2018/0289897 A1 | 10/2018 | Kaneko et al. |
| 2018/0333532 A1 | 11/2018 | Wei |
| 2018/0344939 A1 | 12/2018 | Sakashita |
| 2018/0344940 A1 | 12/2018 | Voytilla |
| 2018/0353682 A1 | 12/2018 | Laurence et al. |
| 2018/0353686 A1 | 12/2018 | Ishikawa et al. |
| 2018/0353687 A1 | 12/2018 | Ishikawa et al. |
| 2018/0353688 A1 | 12/2018 | Ishikawa et al. |
| 2018/0353689 A1 | 12/2018 | Ishikawa et al. |
| 2018/0353690 A1 | 12/2018 | Ishikawa et al. |
| 2018/0353691 A1 | 12/2018 | Ishikawa et al. |
| 2018/0353696 A1 | 12/2018 | Helmer et al. |
| 2018/0369489 A1 | 12/2018 | Nakano et al. |
| 2018/0369506 A1 | 12/2018 | Edwards et al. |
| 2019/0009019 A1 | 1/2019 | Shor et al. |
| 2019/0009027 A1 | 1/2019 | Edwards et al. |
| 2019/0015583 A1 | 1/2019 | Prudden et al. |
| 2019/0015584 A1 | 1/2019 | Meehan et al. |
| 2019/0022305 A1 | 1/2019 | Møller |
| 2019/0022306 A1 | 1/2019 | Gibson et al. |
| 2019/0022312 A1 | 1/2019 | Barmaimon et al. |
| 2019/0022313 A1 | 1/2019 | Barmaimon et al. |
| 2019/0022317 A1 | 1/2019 | Uddin et al. |
| 2019/0035500 A1 | 1/2019 | Saint et al. |
| 2019/0046727 A1 | 2/2019 | Aneas |
| 2019/0083702 A1 | 3/2019 | Nekouzadeh et al. |
| 2019/0143044 A1 | 5/2019 | Paramanandam et al. |
| 2019/0175840 A1 | 6/2019 | Schabbach et al. |
| 2019/0240417 A1 | 8/2019 | Hostettler et al. |
| 2019/0358399 A1 | 11/2019 | Edwards et al. |
| 2019/0374707 A1 | 12/2019 | Damestani et al. |
| 2019/0381238 A1 | 12/2019 | Stonecipher et al. |
| 2020/0009316 A1 | 1/2020 | Cabiri et al. |
| 2020/0061286 A1 | 2/2020 | Giambattista et al. |
| 2020/0078513 A1 | 3/2020 | Wei |
| 2020/0086051 A1 | 3/2020 | Grygus et al. |
| 2020/0114080 A1 | 4/2020 | Barmaimon et al. |
| 2020/0147309 A1 | 5/2020 | Quinn et al. |
| 2020/0155759 A1 | 5/2020 | Hanson et al. |
| 2020/0164155 A1 | 5/2020 | Mojarrad et al. |
| 2020/0171236 A1 | 6/2020 | McCullough et al. |
| 2020/0188580 A1 | 6/2020 | Gregory et al. |
| 2020/0188581 A1 | 6/2020 | Diianni et al. |
| 2020/0197621 A1 | 6/2020 | Quinn et al. |
| 2020/0206429 A1 | 7/2020 | Hering et al. |
| 2020/0215273 A1 | 7/2020 | Gibson et al. |
| 2020/0230323 A1 | 7/2020 | Tan-Malecki et al. |
| 2020/0238006 A1 | 7/2020 | Groszmann et al. |
| 2020/0253525 A1 | 8/2020 | Zhang et al. |
| 2020/0254172 A1 | 8/2020 | Forster et al. |
| 2020/0254181 A1 | 8/2020 | Mosebach et al. |
| 2020/0261643 A1 | 8/2020 | Boyaval et al. |
| 2020/0261648 A1 | 8/2020 | Groszmann et al. |
| 2020/0261652 A1 | 8/2020 | Cowe et al. |
| 2020/0268969 A1 | 8/2020 | McCullough et al. |
| 2020/0297927 A1 | 9/2020 | Conrath et al. |
| 2020/0316290 A1 | 10/2020 | Bourelle et al. |
| 2020/0316291 A1 | 10/2020 | Gibson et al. |
| 2020/0330701 A1 | 10/2020 | Cole et al. |
| 2020/0345943 A1 | 11/2020 | Gazeley et al. |
| 2020/0353160 A1 | 11/2020 | McCullough |
| 2020/0353169 A1 | 11/2020 | McCullough et al. |
| 2020/0353180 A1 | 11/2020 | Edwards et al. |
| 2020/0360612 A1 | 11/2020 | Gazeley et al. |
| 2020/0368447 A1 | 11/2020 | Yigal et al. |
| 2020/0369760 A1 | 11/2020 | Liu et al. |
| 2020/0384207 A1 | 12/2020 | Egesborg et al. |
| 2020/0397995 A1 | 12/2020 | Cronenberg et al. |
| 2020/0397997 A1 | 12/2020 | Hansen et al. |
| 2020/0405948 A1 | 12/2020 | Barmaimon et al. |
| 2020/0405949 A1 | 12/2020 | Yigal et al. |
| 2020/0405950 A1 | 12/2020 | Burren et al. |
| 2020/0405951 A1 | 12/2020 | Burren et al. |
| 2020/0405952 A1 | 12/2020 | Rytz et al. |
| 2021/0003582 A1 | 1/2021 | Kang et al. |
| 2021/0015996 A1 | 1/2021 | Winheim et al. |
| 2021/0016007 A1 | 1/2021 | Baker et al. |
| 2021/0030963 A1 | 2/2021 | Dasbach et al. |
| 2021/0046182 A1 | 2/2021 | Kleppe et al. |
| 2021/0046244 A1 | 2/2021 | O'Connor et al. |
| 2021/0060255 A1 | 3/2021 | Mathews et al. |
| 2021/0069410 A1 | 3/2021 | Destefano et al. |
| 2021/0077725 A1 | 3/2021 | Tschirren et al. |
| 2021/0100955 A1 | 4/2021 | Stettler et al. |
| 2021/0100959 A1 | 4/2021 | Mccaffrey et al. |
| 2021/0100961 A1 | 4/2021 | Brereton et al. |
| 2021/0138147 A1 | 5/2021 | Falkovich |
| 2021/0138157 A1 | 5/2021 | Bar-El et al. |
| 2021/0154407 A1 | 5/2021 | Hirschel et al. |
| 2021/0162126 A1 | 6/2021 | Barkhuff et al. |
| 2021/0178057 A1 | 6/2021 | Cronenberg et al. |
| 2021/0178060 A1 | 6/2021 | Salter et al. |
| 2021/0178073 A1 | 6/2021 | Goldin et al. |
| 2021/0178074 A1 | 6/2021 | Anderson et al. |
| 2021/0196892 A1 | 7/2021 | Dasbach et al. |
| 2021/0213194 A1 | 7/2021 | Cole et al. |
| 2021/0213206 A1 | 7/2021 | Brereton et al. |
| 2021/0220552 A1 | 7/2021 | Barmaimon et al. |
| 2021/0244894 A1 | 8/2021 | Edwards et al. |
| 2021/0252146 A1 | 8/2021 | Cao et al. |
| 2021/0338938 A1 | 11/2021 | Harrison et al. |
| 2021/0353861 A1 | 11/2021 | Rose et al. |
| 2021/0353911 A1 | 11/2021 | Cole |
| 2021/0369952 A1 | 12/2021 | Sasaki |
| 2021/0369957 A1 | 12/2021 | Wieser et al. |
| 2021/0393871 A1 | 12/2021 | Streit et al. |
| 2021/0393873 A1 | 12/2021 | Streit et al. |
| 2021/0402083 A1 | 12/2021 | Gibson et al. |
| 2022/0008652 A1 | 1/2022 | Nekouzadeh et al. |
| 2022/0016347 A1 | 1/2022 | Le Masne et al. |
| 2022/0023544 A1 | 1/2022 | Anderson et al. |
| 2022/0031940 A1 | 2/2022 | Hulliger et al. |
| 2022/0054741 A1 | 2/2022 | Laurence et al. |
| 2022/0080108 A1 | 3/2022 | Pizzochero et al. |
| 2022/0080125 A1 | 3/2022 | Bar-El et al. |
| 2022/0105275 A1 | 4/2022 | Jiang |
| 2022/0133993 A1 | 5/2022 | Smith |
| 2022/0152296 A1 | 5/2022 | Wei |
| 2022/0152308 A1 | 5/2022 | Tan-Malecki et al. |
| 2022/0160960 A1 | 5/2022 | Scott et al. |
| 2022/0160964 A1 | 5/2022 | Besson |
| 2022/0168501 A1 | 6/2022 | Cole |

(56) References Cited

U.S. PATENT DOCUMENTS

| | | |
|---|---|---|
| 2022/0176033 A1 | 6/2022 | Schabbach et al. |
| 2022/0184316 A1 | 6/2022 | Bayer et al. |
| 2022/0184318 A1 | 6/2022 | Rahbari et al. |
| 2022/0193343 A1 | 6/2022 | Burgess et al. |
| 2022/0203032 A1 | 6/2022 | Halbig et al. |
| 2022/0211938 A1 | 7/2022 | Diianni et al. |
| 2022/0218900 A1 | 7/2022 | Gibson et al. |
| 2022/0233775 A1 | 7/2022 | Hassan |
| 2022/0241497 A1 | 8/2022 | Burren et al. |
| 2022/0257862 A1 | 8/2022 | McCullough et al. |
| 2022/0257864 A1 | 8/2022 | Paramanandam et al. |
| 2022/0273866 A1 | 9/2022 | Cabiri et al. |
| 2022/0273878 A1 | 9/2022 | McCullough et al. |
| 2022/0280385 A1 | 9/2022 | Converse et al. |
| 2022/0288314 A1 | 9/2022 | Rioux et al. |
| 2022/0313902 A1 | 10/2022 | Gonnelli et al. |
| 2022/0313925 A1 | 10/2022 | Clasen |
| 2022/0318455 A1 | 10/2022 | Kenyon |
| 2022/0339348 A1 | 10/2022 | Othel-Jacobsen |
| 2022/0362458 A1 | 11/2022 | Schrul et al. |
| 2022/0370715 A1 | 11/2022 | Vatelmacher et al. |
| 2022/0387705 A1 | 12/2022 | Bourelle et al. |
| 2022/0401642 A1 | 12/2022 | Giambattista et al. |
| 2022/0401657 A1 | 12/2022 | Krulevitch et al. |
| 2023/0038182 A1 | 2/2023 | Kunaparaju et al. |
| 2023/0074484 A1 | 3/2023 | Zoda et al. |
| 2023/0076855 A1 | 3/2023 | Edwards et al. |
| 2023/0090486 A1 | 3/2023 | Stefanov et al. |
| 2023/0096391 A1 | 3/2023 | Chen et al. |
| 2023/0101280 A1 | 3/2023 | Barmaimon et al. |
| 2023/0105585 A1 | 4/2023 | Grygus et al. |
| 2023/0122652 A1 | 4/2023 | Breingan et al. |
| 2023/0128850 A1 | 4/2023 | Marcoz et al. |
| 2023/0130563 A1 | 4/2023 | Richards et al. |
| 2023/0145128 A1 | 5/2023 | Demirozer et al. |
| 2023/0149632 A1 | 5/2023 | Grygus |
| 2023/0233755 A1 | 7/2023 | Smith |
| 2023/0241310 A1 | 8/2023 | Stewart et al. |
| 2023/0285664 A1 | 9/2023 | Buri |
| 2023/0285680 A1 | 9/2023 | Huang |
| 2023/0293818 A1 | 9/2023 | Johnson et al. |
| 2024/0033445 A1 | 2/2024 | Günay et al. |
| 2024/0033446 A1 | 2/2024 | Günay et al. |
| 2024/0066216 A1 | 2/2024 | Pizzochero et al. |
| 2024/0148965 A1 | 5/2024 | Scheurer et al. |
| 2024/0325631 A1 | 10/2024 | Streit |
| 2024/0382681 A1 | 11/2024 | Grygus |

FOREIGN PATENT DOCUMENTS

| | | | |
|---|---|---|---|
| CA | 2669616 A1 | 5/2008 |
| CA | 2669616 C | 6/2016 |
| CH | 144526 A | 1/1931 |
| CL | 201903061 | 3/2020 |
| CL | 202201235 | 11/2022 |
| CL | 202301857 | 6/2023 |
| CL | 202301861 | 6/2023 |
| CL | 202301862 | 6/2023 |
| CL | 202301863 | 6/2023 |
| CL | 202301864 | 6/2023 |
| CN | 1026391 C | 11/1994 |
| CN | 101132822 A | 2/2008 |
| CN | 101516424 A | 8/2009 |
| CN | 101531585 A | 9/2009 |
| CN | 102015011 A | 4/2011 |
| CN | 102149416 A | 8/2011 |
| CN | 102665795 A | 9/2012 |
| CN | 103118723 A | 5/2013 |
| CN | 103167887 A | 6/2013 |
| CN | 103619378 A | 3/2014 |
| CN | 103648550 A | 3/2014 |
| CN | 104602733 A | 5/2015 |
| CN | 104602735 A | 5/2015 |
| CN | 105263562 A | 1/2016 |
| CN | 105413021 A | 3/2016 |
| CN | 306715264 S | 7/2021 |
| CO | 6920282 A2 | 4/2014 |
| EM | 0013712800001 | 5/2013 |
| EM | 0031477760001 | 5/2016 |
| EM | 0038141020001 | 3/2017 |
| EM | 0038141020004 | 3/2017 |
| EM | 0072576210001 | 11/2019 |
| EP | 1002551 A2 | 5/2000 |
| EP | 1219283 A3 | 12/2002 |
| EP | 1284758 A2 | 2/2003 |
| EP | 1064035 B1 | 11/2003 |
| EP | 1518575 A1 | 3/2005 |
| EP | 1646412 B1 | 3/2007 |
| EP | 1920793 A1 | 5/2008 |
| EP | 1465689 B1 | 9/2009 |
| EP | 1855754 B1 | 9/2009 |
| EP | 1696981 B1 | 10/2009 |
| EP | 2219710 B1 | 4/2011 |
| EP | 2396058 A1 | 12/2011 |
| EP | 2301611 B1 | 8/2012 |
| EP | 2608825 B1 | 8/2014 |
| EP | 2689516 B1 | 5/2015 |
| EP | 2946800 A1 | 11/2015 |
| EP | 2571549 B1 | 2/2016 |
| EP | 2300078 B1 | 3/2016 |
| EP | 3000497 A3 | 7/2016 |
| EP | 2902060 B1 | 9/2016 |
| EP | 2736565 B1 | 7/2017 |
| EP | 3260146 A1 | 12/2017 |
| EP | 3260147 A1 | 12/2017 |
| EP | 3260149 A1 | 12/2017 |
| EP | 3260151 A1 | 12/2017 |
| EP | 2929900 B1 | 2/2019 |
| EP | 3852840 A1 | 7/2021 |
| EP | 3862038 A1 | 8/2021 |
| EP | 2731641 B1 | 9/2021 |
| EP | 3705149 B1 | 9/2021 |
| EP | 3233163 B1 | 10/2021 |
| EP | 3630227 B1 | 11/2021 |
| EP | 3925643 A1 | 12/2021 |
| EP | 3928812 A1 | 12/2021 |
| EP | 3077022 B1 | 1/2022 |
| EP | 3618895 B1 | 4/2022 |
| EP | 3760253 B1 | 4/2022 |
| EP | 3714922 B1 | 5/2022 |
| EP | 3756704 B1 | 5/2022 |
| EP | 3664864 B1 | 6/2022 |
| EP | 4029545 A1 | 7/2022 |
| EP | 3658203 B1 | 8/2022 |
| EP | 2991711 B1 | 10/2022 |
| EP | 3256189 B1 | 10/2022 |
| EP | 4088761 A1 | 11/2022 |
| EP | 3549524 B1 | 1/2023 |
| EP | 3268065 B1 | 5/2023 |
| EP | 3474926 B1 | 5/2023 |
| FR | 1137035 A | 5/1957 |
| GB | 190220334 A | 7/1903 |
| GB | 376973 A | 7/1932 |
| GB | 2064964 A | 6/1981 |
| GB | 2396298 A | 6/2004 |
| GB | 2467904 A | 8/2010 |
| GB | 0229384 | 1/2023 |
| IN | 3612DELNP2010 A | 11/2011 |
| JP | S4876390 A | 10/1973 |
| JP | S645565 A | 1/1989 |
| JP | H03250270 A | 11/1991 |
| JP | H06207644 A | 7/1994 |
| JP | H07501234 A | 2/1995 |
| JP | H0852213 A | 2/1996 |
| JP | 2003527159 A | 9/2003 |
| JP | 2005-508231 A | 3/2005 |
| JP | 2005058415 A | 3/2005 |
| JP | 2005145384 A | 6/2005 |
| JP | 2005524447 A | 8/2005 |
| JP | 2005534433 A | 11/2005 |
| JP | 2009-505720 A | 2/2009 |
| JP | 2011508634 A | 3/2011 |
| JP | 2013529520 A | 7/2013 |
| JP | 2014510573 A | 5/2014 |

(56)    References Cited

FOREIGN PATENT DOCUMENTS

| | | | |
|---|---|---|---|
| JP | 2014124452 A | | 7/2014 |
| JP | 2014-526938 A | | 10/2014 |
| JP | 1692548 S | | 8/2021 |
| JP | 1736157 S | | 2/2023 |
| JP | 1736158 S | | 2/2023 |
| JP | 1736189 S | | 2/2023 |
| JP | 1736190 S | | 2/2023 |
| JP | 1743322 S | | 5/2023 |
| JP | 1746594 S | | 6/2023 |
| JP | 1746678 S | | 6/2023 |
| KR | 20040064320 A | | 7/2004 |
| KR | 10-2004-0096561 A | | 11/2004 |
| KR | 10-2005-0092690 A | | 9/2005 |
| KR | 20130137249 A | | 12/2013 |
| KR | 101496207 B1 | | 3/2015 |
| KR | 20160001262 A | | 1/2016 |
| NZ | 576654 A | | 7/2012 |
| RU | 2127131 C1 | | 3/1999 |
| RU | 2573042 C2 | | 1/2016 |
| RU | 2580481 C2 | | 4/2016 |
| TW | D211147 S | | 4/2021 |
| WO | WO-9407553 A1 | | 4/1994 |
| WO | WO-9907425 A1 | | 2/1999 |
| WO | WO-0020058 A1 | | 4/2000 |
| WO | 02/055128 A2 | | 7/2002 |
| WO | WO-03024511 A1 | | 3/2003 |
| WO | WO-03092771 A1 | | 11/2003 |
| WO | WO-2004044464 A1 | | 5/2004 |
| WO | WO-2004075955 A1 | | 9/2004 |
| WO | WO-2006061170 A1 | | 6/2006 |
| WO | WO-2006067217 A2 | | 6/2006 |
| WO | WO-2007035621 A1 | | 3/2007 |
| WO | WO-2007050788 A2 | | 5/2007 |
| WO | WO-2008091838 A2 | | 7/2008 |
| WO | WO-2009024608 A1 | | 2/2009 |
| WO | WO-2009030974 A1 | | 3/2009 |
| WO | WO-2009030975 A1 | | 3/2009 |
| WO | WO-2009128265 A1 | | 10/2009 |
| WO | WO-2009158613 A1 | | 12/2009 |
| WO | WO-2010029054 A1 | | 3/2010 |
| WO | WO-2010035057 A1 | | 4/2010 |
| WO | WO-2010035059 A1 | | 4/2010 |
| WO | 2011/006877 A1 | | 1/2011 |
| WO | WO-2011014514 A1 | | 2/2011 |
| WO | WO-2011060197 A1 | | 5/2011 |
| WO | WO-2011084951 A2 | | 7/2011 |
| WO | WO-2011095091 A1 | | 8/2011 |
| WO | WO-2011125133 A1 | | 10/2011 |
| WO | WO-2011133823 A1 | | 10/2011 |
| WO | 2011139110 A2 | | 11/2011 |
| WO | WO-2011156373 A1 | | 12/2011 |
| WO | WO-2012032411 A2 | | 3/2012 |
| WO | WO-2012101669 A1 | | 8/2012 |
| WO | WO-2012114105 A1 | | 8/2012 |
| WO | 2012158136 A1 | | 11/2012 |
| WO | WO-2013034647 A1 | | 3/2013 |
| WO | WO-2013077800 A1 | | 5/2013 |
| WO | WO-2013155153 A1 | | 10/2013 |
| WO | WO-2013179137 A2 | | 12/2013 |
| WO | WO-2014037946 A1 | | 3/2014 |
| WO | WO-2014049745 A1 | | 4/2014 |
| WO | WO-2014054535 A1 | | 4/2014 |
| WO | 2014066256 A1 | | 5/2014 |
| WO | WO-2014106096 A1 | | 7/2014 |
| WO | WO-2014149357 A1 | | 9/2014 |
| WO | 2014185681 A1 | | 11/2014 |
| WO | WO-2015024960 A1 | | 2/2015 |
| WO | WO-2015055747 A1 | | 4/2015 |
| WO | WO-2015081337 A2 | | 6/2015 |
| WO | WO-2015123688 A1 | | 8/2015 |
| WO | WO-2015143058 A1 | | 9/2015 |
| WO | WO-2015164647 A1 | | 10/2015 |
| WO | WO-2015164648 A1 | | 10/2015 |
| WO | WO-2015185176 A1 | | 12/2015 |
| WO | WO-2015187793 A1 | | 12/2015 |
| WO | 2016033496 A1 | | 3/2016 |
| WO | WO-2016041871 A1 | | 3/2016 |
| WO | WO-2016041873 A1 | | 3/2016 |
| WO | WO-2016049532 A1 | | 3/2016 |
| WO | WO-2016052332 A1 | | 4/2016 |
| WO | WO-2016053954 A1 | | 4/2016 |
| WO | WO-2016074850 A1 | | 5/2016 |
| WO | WO-2016091841 A1 | | 6/2016 |
| WO | WO-2016100055 A1 | | 6/2016 |
| WO | WO-2016100781 A1 | | 6/2016 |
| WO | WO-2016115372 A1 | | 7/2016 |
| WO | WO-2016130679 A2 | | 8/2016 |
| WO | 2016149038 A1 | | 9/2016 |
| WO | WO-2016141082 A1 | | 9/2016 |
| WO | 2016157638 A1 | | 10/2016 |
| WO | WO-2016210404 A1 | | 12/2016 |
| WO | WO-2017037468 A1 | | 3/2017 |
| WO | WO-2017050781 A1 | | 3/2017 |
| WO | 2014/049712 A1 | | 4/2017 |
| WO | WO-2017062943 A2 | | 4/2017 |
| WO | WO-2017089271 A1 | | 6/2017 |
| WO | WO-2017089287 A1 | | 6/2017 |
| WO | WO-2017089288 A1 | | 6/2017 |
| WO | WO-2017139003 A1 | | 8/2017 |
| WO | WO-2017139573 A1 | | 8/2017 |
| WO | WO-2017139741 A1 | | 8/2017 |
| WO | WO-2017141255 A1 | | 8/2017 |
| WO | WO-2017219156 A1 | | 12/2017 |
| WO | WO-2017219157 A1 | | 12/2017 |
| WO | WO-2017219158 A1 | | 12/2017 |
| WO | WO-2018015749 A2 | | 1/2018 |
| WO | WO-2018100201 A1 | | 6/2018 |
| WO | WO-2018130944 A1 | | 7/2018 |
| WO | WO-2018144056 A1 | | 8/2018 |
| WO | WO-2018164829 A1 | | 9/2018 |
| WO | WO-2018204779 A1 | | 11/2018 |
| WO | WO-2018222521 A1 | | 12/2018 |
| WO | WO-2019018169 A1 | | 1/2019 |
| WO | WO-2020058069 A1 | | 3/2020 |
| WO | WO-2020173993 A1 | | 9/2020 |
| WO | WO-2020219127 A1 | | 10/2020 |
| WO | WO-2021012852 A1 | | 1/2021 |
| WO | 2021093327 A1 | | 5/2021 |
| WO | WO-2021222057 A1 | | 11/2021 |
| WO | WO-2021224388 A1 | | 11/2021 |
| WO | WO-2021233982 A1 | | 11/2021 |
| WO | WO-2022072809 A1 | | 4/2022 |
| WO | WO-2022088501 A1 | | 5/2022 |
| WO | WO-2022097057 A1 | | 5/2022 |
| WO | WO-2022116603 A1 | | 6/2022 |
| WO | WO-2022121945 A1 | | 6/2022 |
| WO | WO-2022147166 A1 | | 7/2022 |
| WO | WO-2022147985 A1 | | 7/2022 |
| WO | WO-2022148048 A1 | | 7/2022 |
| WO | WO-2022159242 A1 | | 7/2022 |
| WO | WO-2022212239 A1 | | 10/2022 |
| WO | WO-2022212713 A2 | | 10/2022 |
| WO | WO-2022271950 A1 | | 12/2022 |
| WO | WO-2023272784 A1 | | 1/2023 |
| WO | 2023150090 A1 | | 8/2023 |
| WO | 2023187749 A1 | | 10/2023 |
| WO | 2024052442 A1 | | 3/2024 |
| WO | 2024053149 A1 | | 3/2024 |
| WO | 2024068801 A1 | | 4/2024 |
| WO | 2024069630 A1 | | 4/2024 |

OTHER PUBLICATIONS

International Search Report and Written Opinion mailed Sep. 3, 2024 in International Application No. PCT/US2024/029802, 12 pages.
International Search Report and Written Opinion mailed Sep. 19, 2024 in International Application No. PCT/US2024/029801, 12 pages.
BD Libertas, Wearable Injector, BD Drug Delivery Systems, drugdeliverysystems.bd.com, Accessed Jun. 26, 2023.
Chinese Office Action for Chinese Application No. 201680027080.7 mailed on Sep. 4, 2019, 9 pages.

(56) References Cited

OTHER PUBLICATIONS

Chinese Notice of Allowance mailed Mar. 3, 2022 in Chinese Application No. 20188027244.5 (7 pages).

Dia Tribe, Making Sense of Diabetes, Calibre Finesse Bolus Insulin Patch Pump to Launch in the US in 2016, 2016, [retrieved on Nov. 22, 2016]. Retrieved from the Internet: (URL: https://diatribe.org/calibra-finesse-bolus-insulin-patch-pump-launch-us-2016 ), 1 Page.

Diabetes, The Healthy Living Magazine, How Insulin Pumps Work, an inside look at insulin pump technology, by Erika Gebel Berg, PhD, Sep. 2014, [Retrieved on Nov. 22, 2016], retrieved from the Internet: (URL: http://www.diabetesforecast.org/2014/09-sep/how-insulin-pumps-work.html ), 2016 American Diabetes Association, 6 pages.

Drug Delivery Performance and Antibody Viability after gas powered plunger injection, PODD, altaviz, Oct. 15, 2018, 15 pages.

English Translation of the Preliminary Office Action Report Related to Brazilian Patent Application No. BR112019020705-8, Sep. 19, 2022 (2 pages).

Eurasian Patent Office Search Report issued in Eurasian Application No. 202290947 on Sep. 8, 2022 (3 pages).

European Examination Report for Application No. 16713195.2, mailed on Aug. 10, 2018, 8 pages.

European search report for European Application No. 20198799.7 mailed on Dec. 21, 2020, 8 pages.

Extended European Search Report for European Application No. 22160171.9 mailed on Aug. 25, 2022, 8 pages.

International Search Report for Application No. PCT/US2018/031077 mailed on Sep. 17, 2018, 5 pages.

International Search Report and Written Opinion for Application No. PCT/2022/079921, mailed on May 23, 2023, 32 pages.

Invitation to Pay Additional Fees and, Where Applicable, Protest Fee for Application No. PCT/US2022/079921, mailed Mar. 24, 2023, 15 pages.

Japanese Office Action in corresponding Japanese Application No. 2017-547515, mailed on Dec. 24, 2019, 5 pages.

Medicom Innovation Partner, Flexible Wearable Patch Pump, Wearable Injectors, OndrugDelivery Magazine, Issue 78, www.issuu.com, 2017 (1 page).

Sorrel Medical, Your Way to Deliver More, PODD, 2018, 18 pages.

Verjans et al. "A New Concept in Aseptic Filling: Closed-Vial Technology", Pharmaceutical Technology, May 2005, 4 pages.

Very Well, What is the V-GO Insulin Patch Pump?, Valeritas V-GO Disposable Insulin Device, Retrieved on Nov. 22, 2016], retrieved from the Internet: (URL: http://www.verywell.com/what-is-an-Insulin-Patch-Pump-1067254 ), 9 pages.

West Pharmaceutical Services, E3D, OBI-1 Wearable Injector, on Body Injector, Elcam Drug Delivery Services, www.issuu.com, 2019 (1 page).

West Pharmaceutical Services, Pharmapack 2021: Gerresheimer with Innocative SensAIR Platform for a Drug Delivery Device for Biologics, Sensair, Gerresheimer's Group, Pharmaceutical Technology, www.issuu.com, 2022 (1 page).

West Pharmaceutical Services, SmartDose® on-Body Delivery System Platform (OBDS), www.issuu.com, 2017 (1 page).

West Pharmaceutical Services, SmartDose® on-Body Delivery System, West, www.issuu.com, 2019 (1 page).

West Pharmaceutical Services, Wearable Drug Delivery Device, Eitan Sorrel Medical, www.issuu.com, 2019 (1 page).

Ypsomed, Ypsodose, Delivery Systems, yds.ypsomed.com, Webpage last updated Jun. 4, 2022 (1 page).

International Preliminary Report on Patentability mailed May 30, 2024 in International Application No. PCT/US2022/079921 23 pages).

International Search Report and Written Opinion mailed Sep. 30, 2024 in International Application No. PCT/US2024/034116 (10 pages).

Invitation to Pay Additional Fees and, Where Applicable, Protest Fee, mailed Oct. 2, 2024, in International Application No. PCT/US2024/034114 (15 pages).

International Search Report and Written Opinion of International Application PCT/US2025/030352, mailed on Oct. 9, 2025. (12 pages).

* cited by examiner

100

107

111

106

102

103

104

MEDICAL DEVICE PACKAGING AND RELATED METHODS

CROSS-REFERENCE TO RELATED APPLICATIONS

This application claims the benefit of priority from U.S. Provisional Patent Application No. 63/508,812, filed Jun. 16, 2023, which is incorporated by reference herein.

FIELD OF THE DISCLOSURE

Various embodiments of the present disclosure relate to packaging for a medical device. Embodiments of the disclosure may include a packaging for housing a drug delivery device, e.g., an auto-injector.

INTRODUCTION

Many medical devices are packaged for distribution to healthcare facilities and/or for storage, for example. Once a user, e.g., a healthcare provider, is ready to use the medical device, the medical device is removed from the packaging and prepped, if necessary, for use on a patient. In order to remove medical devices from packaging, users often need to directly handle the devices and to push, pull, lift, slide, or otherwise directly touch the medical device with their hands. In some instances, it may not be desirable to handle the medical devices too much, e.g., for reasons of sterility or to inhibit damage to the medical devices, when removing the medical devices from their packaging. For example, auto-injectors may be contaminated when they are handled during removal of packaging, which may jeopardize the sterility of the components of the auto-injector, e.g., a chamber, syringe, needle, needle attachment, and/or any medicament or other fluid contained within.

SUMMARY

In one aspect, the present disclosure describes a packaging comprising a tray having a body surrounding an exposed cavity and a groove; a lip surrounding the opening, wherein the lip extends radially outward from the cavity and defines a periphery of the tray; a retainer for covering a portion of the opening of the tray, the retainer having an aperture, wherein the aperture corresponds to the groove of the tray; a removable cover; and an auto-injector contained within the cavity, wherein the auto-injector is pre-filed with a medicament or other fluid.

Various embodiments of the packaging may include one or more of the following aspects. The packaging may include a gaseous sterilant. The packaging may include a gaseous sterilant including one or more of ethylene oxide, vaporized hydrogen peroxide, ethyl alcohol, nitrous oxide, or nitrogen dioxide. The tray may include a first plurality of sidewalls and a second plurality of sidewalls. The packaging may include a lug. The lip may include an adhesive and may form a seal with the retainer to enclose the auto-injector within the cavity. The tray and/or the retainer may include one or more of polypropylene, polystyrene, polyethylene, polycarbonate, polyvinyl chloride, or polyethylene terephthalate glycol. The removable cover may include high-density polyethylene fibers, thermoplastic materials, or a combination thereof. The medicament or fluid may comprise one or more of dupilumab and cemiplimab.

In another aspect, the present disclosure describes a packaging for an auto-injector, the packaging comprising a tray having an opening and a cavity; a lip surrounding the opening, wherein the lip extends radially outward from the cavity and defines a periphery of the tray; a removable cover having a periphery that is adhered to the lip; and a retainer for covering a portion of the opening of the tray.

Various embodiments of the packaging may include one or more of the following aspects. The removable cover may be permeable to a gaseous sterilant. The gaseous sterilant may include one or more of ethylene oxide, vaporized hydrogen peroxide, ethyl alcohol, nitrous oxide, or nitrogen dioxide. The tray and/or of the retainer may include one or more of polypropylene, polystyrene, polyethylene, polycarbonate, polyvinyl chloride, or polyethylene terephthalate glycol. The removable cover may include high-density polyethylene fibers, thermoplastic materials, or a combination thereof. The auto-injector may contain a medicament comprising one or more of dupilumab and cemiplimab.

In another aspect, the present disclosure describes a method of removing an externally-sterilized auto-injector from a packaging, the packaging including a tray having an opening and a cavity, a retainer, a removable cover, and a gaseous sterilant, the method comprising: removing the removable cover to expose the retainer; removing the retainer to expose the cavity of the tray; grasping a portion of the externally-sterilized auto-injector held within the cavity of the tray; and ejecting the externally-sterilized auto-injector from the tray.

Various embodiments of the method may include one or more of the following aspects. The method may include pushing a portion of the tray towards the cavity of the tray, wherein pushing the portion of the tray causes a portion of the tray to flex. Pushing the portion of the tray may cause the externally-sterilized auto-injector to release from the cavity of the tray. The gaseous sterilant may include one or more of ethylene oxide, vaporized hydrogen peroxide, ethyl alcohol, nitrous oxide, or nitrogen dioxide. The externally-sterilized auto-injector may contain a medicament comprising one or more of dupilumab and cemiplimab

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment (s).

Figure 1:
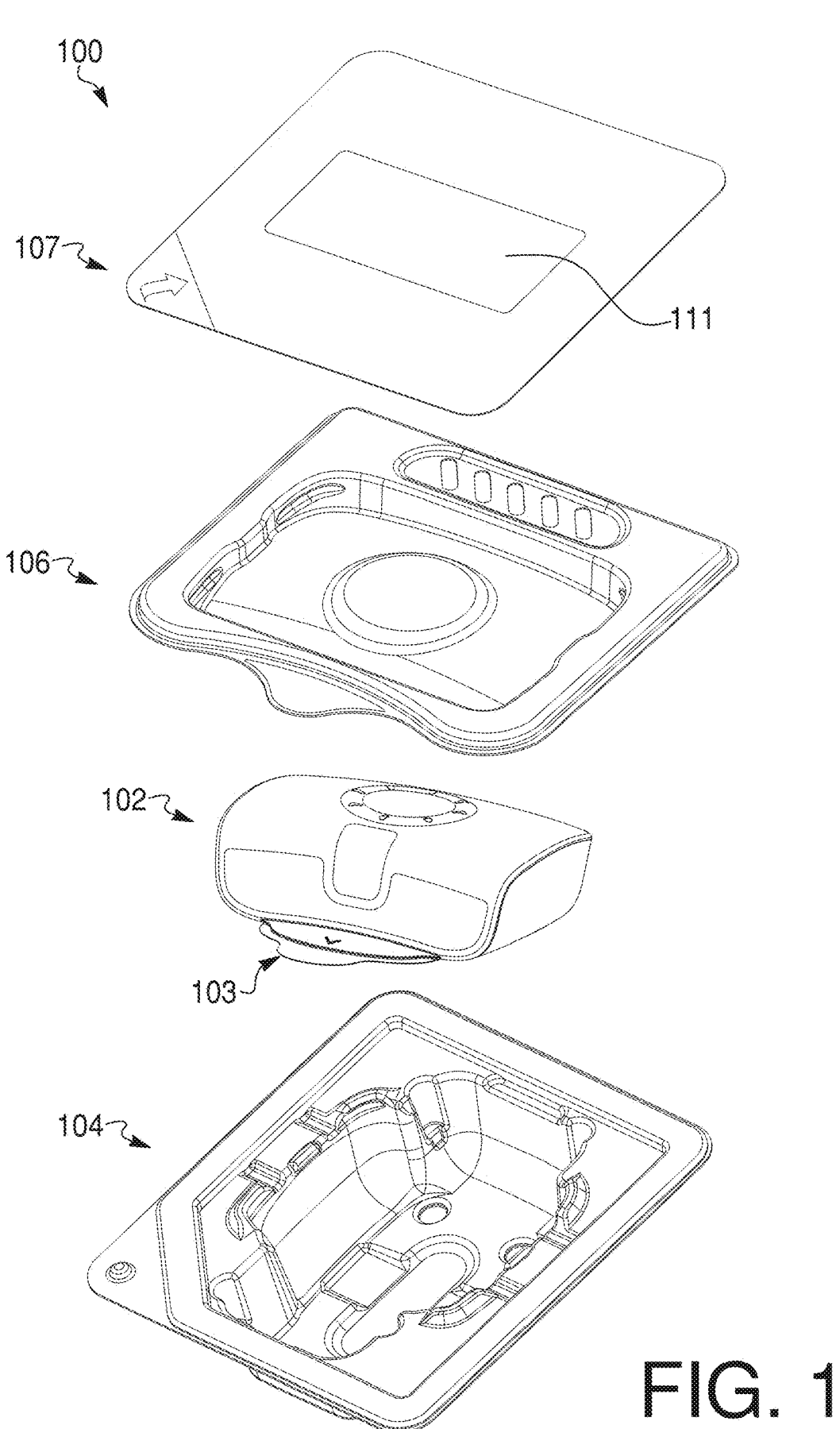
FIG. 1 provides a perspective view of an exemplary packaging, according to an embodiment of the present disclosure.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items. Further, as used herein, the terms "about," "substantially," and "approximately" generally mean +/−10% of the indicated value.

As used in the present disclosure, the term "sterilization" refers to achieving a level of sterility appropriate for a formulated drug substance or drug product for commercial distribution and use. More particularly, "sterilization" as used herein includes, but is not limited to, achieving a level of sterility that sterilizes a drug delivery device while packaged within, e.g., a packaging according to aspects of the present disclosure, for commercial distribution and use. Such a level of sterility may be defined in, for example, regulatory guidelines or regulations, such as guidelines released by the U.S. Food and Drug Administration. In some embodiments, such a level of sterility may include, for example, a 6-log reduction in microbial populations of biological indicators placed on an outside or inside surface of a drug product (e.g., an outside surface of an auto-injector or an inside surface of a blister pack). In other embodiments, such a level of sterility may include, for example, a 9-log or 12-log reduction in microbial populations of biological indicators. Sterilization refers to achieving such an appropriate level of sterility while also achieving a sufficiently low level of residual sterilizing chemicals (e.g., vaporized hydrogen peroxide, ethylene oxide, nitrogen dioxide ($NO_2$), nitric oxide (NO), etc.) for commercial distribution and use. Such a low level of residual sterilizing chemical may also be defined in regulatory guidelines or regulations.

As used in the present disclosure, the term "external sterilization" refers to the sterilization of a drug delivery device in a container or packaging, such as in a primary packaging component, or in both primary and secondary packaging components, suitable for commercial distribution and use. External sterilization may include, but is not limited to, terminal sterilization, as readily understood by those of ordinary skill in the art.

DETAILED DESCRIPTION

Embodiments of the present disclosure relate to medical device packaging, and, in particular, to packaging for auto-injectors. In some embodiments, instead of a functional auto-injector, it could be a training device that is identical in outer dimensions but is otherwise not able to deliver a medicament. In some embodiments, the packaging may be configured to contain externally-sterilized (or terminally-sterilized) auto-injectors. In particular, embodiments of the disclosure may be directed to packaging for externally-sterilized (or terminally-sterilized) auto-injectors containing medicaments or other fluids (e.g., placebo). Exemplary auto-injectors may be pre-filled with, e.g., 50 mL or less, 20 mL or less, 15 mL or less, 10 mL or less, 5 mL or less, or 1 ml or less of an medicament or other fluids e.g., (placebo). Exemplary auto-injectors are described in U.S. Pat. No. 10,182,969 B2, U.S. Pat. No. 11,406,565 B2, US 2022/0401302A1, WO 2018/204779 A1, and WO 2023/091922 A2, which are incorporated by reference herein in their entireties. The packaging may include one or more features to facilitate removal of a medical device from the packaging. For example, the packaging may include features that allow a user to pull the auto-injector up and out of the packaging with minimal disturbance to the auto-injector or its plunger/ needle, and/or impact on the sterility of the auto-injector. The packaging may include one or more deformable projections or portions that may be inverted, pushed, and/or otherwise deformed in order to dislodge, eject, push, or otherwise move the medical device to release it from the packaging. The packaging may also be flexible to allow a user to push on the projection to bend or flex the packaging to promote release of the medical device contained within.

FIG. 1 depicts components of an exemplary packaging 100 for a medical device 102. Specifically, FIG. 1 depicts a tray 104, a retainer 106, and a removable cover 107. Each component of packaging 100 will be discussed in further detail. As shown in FIG. 1, medical device 102 may fit into an opening of tray 104 and retainer 106 may be configured to be secured to a portion of tray 104 via a friction fit, such that tray 104 and retainer 106 form an enclosure around medical device 102 and close an opening of tray 104. Removable cover 107 may be configured to attach to a portion of tray 104, e.g., via an adhesive. While the figures depict aspects where tray 104 and retainer 106 are formed as discreet components configured to be complementary to one another, those of ordinary skill in the art will readily recognize that the tray and retainer may be made of a suitable unitary or one-piece construction. In such embodiments, packaging 100 may include a hinge, e.g., a joint, fulcrum, or any appropriate connector. In such embodiments, retainer 106 may be connected to tray 104 via a hinge allowing retainer 106 to rotate about the hinge connection to open or close the opening of tray 104, e.g., in a clamshell configuration. In further aspects, the hinge connection feature may be selectively frangible.

To facilitate removal of medical device 102 from packaging 100, a user may remove removable cover 107 from a portion of tray 104, and then remove retainer 106 from a portion of tray 104, exposing medical device 102. A user may then orient tray 104 such that an opening of tray 104 is angled toward a surface onto which medical device 102 is to be ejected. Medical device 102 may then be ejected from tray 104. A user may also push on and/or flex a portion of tray 104 to eject medical device 102 from tray 104. For example, the user may push on and/or flex a portion of tray 104 and turn tray 104 sideways or up-side-down in order to discharge medical device 102 from tray 104 and onto a sterile surface, e.g., a sterile table, tray, cloth, liner, etc. Flexure of tray 104 while an opening of tray 104 is angled gravitationally downward may cause medical device 102 to be released, e.g., ejected, out of the packaging onto a surface with the user contacting only the packaging and not directly contacting medical device 102.

Packaging 100 may include tray 104, in which the auto-injector is contained during storage, and a lip 110 extending around a perimeter of tray 104 and defining an opening in tray 104. The top of tray 104 (shown, e.g., in FIGS. 1 and 2) may be covered with retainer 106 (shown, e.g., in FIGS. 1 and 4), which may enclose the auto-injector within tray 104 during sterilization and/or storage. In some embodiments, tray 104 and/or retainer 106 may be sealed with a removable cover 107, which may enclose the medical device, e.g., auto-injector, in tray 104 and/or retainer 106 during sterilization and/or storage. In some embodiments, packaging 100 may be blister packaging, i.e., packaging 100 may be a pre-formed plastic packaging. In some examples, packaging 100 and/or components of packaging 100 may be made from a formable web, such as a thermoformed plastic.

Packaging 100 may be suitable for use with an external (or terminal) sterilization process, e.g., an ethylene oxide (EtO), a vapor hydrogen peroxide (VHP) sterilization process and/or an ethyl alcohol sterilization process. Accordingly, a medical device (e.g., an auto-injector) may be packaged within packaging 100 and then subjected to external sterilization or terminal sterilization. Sterilants, such as VHP, may not affect the medication contained within the auto-injector but may sterilize the exterior surface of the auto-injector. Exemplary sterilization processes are described in WO 2018/182929 A1, which is incorporated by reference herein in its entirety. Materials used in packaging 100 may be semi-permeable to sterilizing agents to allow the sterilizing agents to traverse portions of or all of the packaging to sterilize the exterior of the medical device contained within the packaging, as well as the interior of the packaging, once the medical device is sealed within the packaging. In some embodiments, at least 75%, at least 80%, at least 85%, at least 90%, or at least 95%, of packaging 100 is sterilized. For example, removable cover 107 may be permeable to vapor hydrogen peroxide and/or an ethyl alcohol. Removable cover 107 may be formed of, e.g., Tyvek or other suitable high-density polyethylene fibers, ethylene-vinyl acetate, and/or other thermoplastic materials. Removable cover 107 may also be permeable to a suitable gaseous sterilant, such as ethylene oxide, vaporized hydrogen peroxide, ethyl alcohol, nitrous oxide, nitrogen dioxide, or any appropriate sterilant in the art. Components of packaging 100, e.g., tray 104 and/or retainer 106, may be thermoformed plastic. For example, tray 104 and/or retainer 106 may be formed of polypropylene, polystyrene, polyethylene, polycarbonate, polyvinyl chloride, or polyethylene terephthalate glycol (PETG). Components of packaging 100, e.g., tray 104, retainer 106, and/or removable cover 107, and the size and/or shape of such components may be configured to facilitate high speed manufacturing of packaging 100 and/or improve material distribution of packaging 100.

In some aspects of the present disclosure, packaging 100, e.g., one or more of tray 104, retainer 106, and removable cover 107, discussed herein may be impermeable (or partially permeable or partially impermeable) to one or more suitable gaseous sterilants. In such aspects, it is contemplated that a drug delivery device (e.g., the auto-injector of the present disclosure) may be appropriately packaged within the packaging (e.g., the tray and retainer) of the present disclosure along with a sterilant or source of sterilant (as disclosed in greater detail below), and thereby sealed for delivery by an exemplary removable cover having limited or no permeability to the sterilant. In some embodiments, the sterilant sealed within packaging 100 may be in a gaseous, solid, liquid form, or a combination thereof. Still further, it is contemplated that a source of sterilant may be sealed within packaging 100, wherein the source of sterilant may be a solid apparatus configured to release gaseous sterilant upon a predetermined triggering event or upon the passing of a predetermined time delay. In some aspects, the solid apparatus may include multiple layers or chambers storing ingredients configured to combine and produce a gaseous sterilant, e.g., ethylene oxide, vaporized hydrogen peroxide, ethyl alcohol, nitrous oxide, nitrogen dioxide, or any appropriate sterilant in the art. Still further, the solid apparatus may include a sterilant wafer containing a polymer configured to generate and/or release a suitable gaseous sterilant after packaging 100 has been sealed. Those of ordinary skill in the art will readily recognize that the suitable gaseous sterilant may include any of the gaseous sterilants described herein. In some embodiments, packaging 100, e.g., one or more of tray 104, retainer 106, and removable cover 107, may include an indicator to allow a user to determine whether a component of packaging 100, e.g., one or more of tray 104, retainer 106, and removable cover 107, and its contents have been sterilized. For example, tray 104, retainer 106, and/or removable cover 107 may include an indicator (e.g., a tape or a label) that changes appearance in color or pattern to visually show whether a sterilization process has been performed.

Designing packaging 100 to be used with external sterilization processes and to allow a user to remove the contents of the packaging without directly handling the contents, as described herein, reduces the likelihood that sterility of the contained medical device will be compromised. As a result, packaging 100, as described herein, may also reduce the chance that a person on whom the medical device is used will be infected by the medical device.

An externally-sterilized auto-injector may be one in which any viable organisms on the surface of the auto-injector have been terminated or killed, making them non-viable even though they may remain. Any components of the auto-injector, e.g., a needle mechanism, cartridge, body, etc., may be externally-sterilized. In some aspects, depyrogenation and/or other removal processes may be undertaken prior to external sterilization.

As shown in FIG. 1, device 102 may include an adhesive patch 103. Adhesive patch 103 may be configured to couple to a tissue-engaging surface to help secure device 102 to a user's body (e.g., skin). Adhesive patch 103 may be formed from fabric or any other suitable material, and may include an adhesive. The adhesive may be an aqueous or solvent-based adhesive, or may be a hot melt adhesive, for example. Suitable adhesives also include acrylic based, dextrin based, and urethane based adhesives as well as natural and synthetic elastomers. In some examples, the adhesive provided on patch 103 may be activated upon contact with a user's skin. In yet another example, patch 103 may include a non-woven polyester substrate and an acrylic or silicone adhesive. Patch 103 may be joined to device 102 by, e.g., a double-sided adhesive, or by other mechanisms like ultrasonic welding. Adhesive patch 103 may be externally-sterilized, such that packaging 100 protects the sterility of adhesive patch 103 prior to use of device 102.

Figure 2:
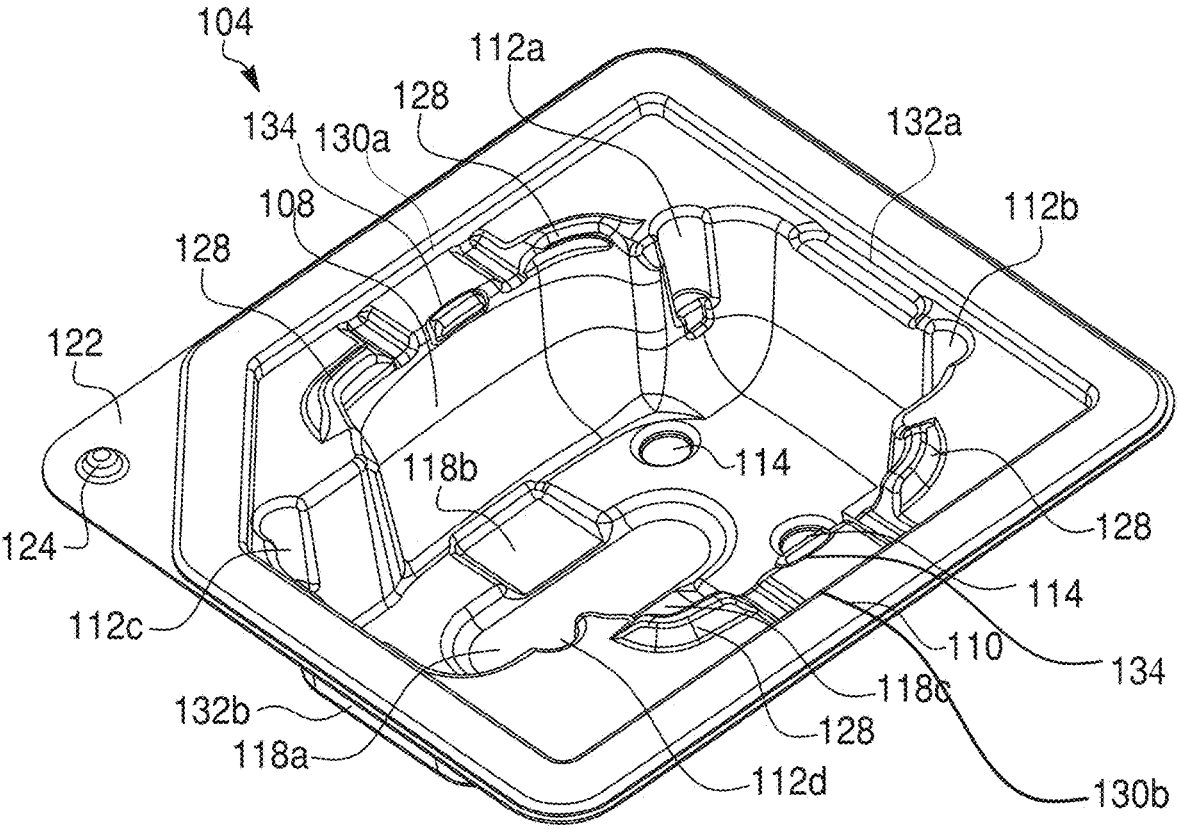
FIG. 2 provides a perspective of an exemplary tray, according to an embodiment of the present disclosure.

FIG. 2 depicts a perspective view of tray 104. Tray 104 may include a cavity 108 configured to contain a portion of an auto-injector. Portions of tray 104 may be shaped to correspond to the shape of device 102, as shown in FIG. 1. For example, portions of tray 104 may be configured such that portions of tray 104 form a friction fit with at least some portions of device 102. In other examples, a portion of tray 104 may be configured to form a friction fit with adhesive patch 103 of device 102 (FIG. 1). Tray 104 and/or components of tray 104 may be made from a formable web, such as a thermoformed plastic. In some embodiments, tray 104 and/or components of tray 104 may be formed of a flexible material. For example, tray 104 and/or components of tray 104 may be formed of one or more of polypropylene, polystyrene, polyethylene, polycarbonate, polyvinyl chloride, or polyethylene terephthalate glycol (PETG).

Referring to FIGS. 2, 3A-3C, and 3F-3H, tray 104 may include a plurality of sidewalls. For example, tray 104 may include a first plurality of sidewalls 130a, 130b and a second plurality of sidewalls 132a, 132b. In some embodiments, a length of first plurality of sidewalls 130a, 130b may be larger than a length of second plurality of sidewalls 132a, 132b. In some embodiments, a length of first plurality of sidewalls 130a, 130b may be less than a length of second plurality of sidewalls 132a, 132b. In some embodiments, a length of first plurality of sidewalls 130a, 130b may be equal to a length of second plurality of sidewalls 132a, 132b.

Figure 3A:
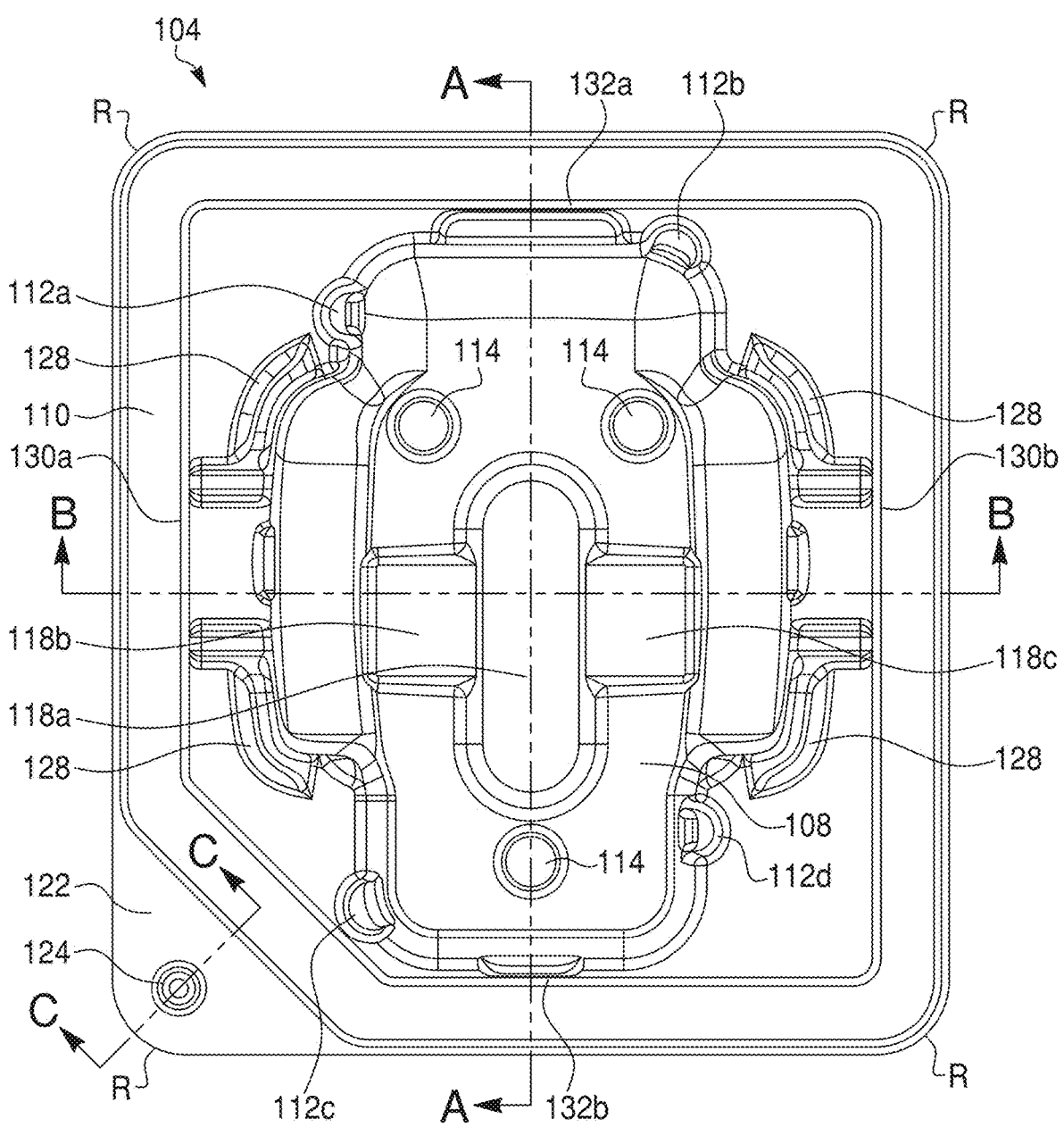
FIGS. 3A-3H provide detailed views of an exemplary tray, according to embodiment of the present disclosure.
Figure 3B:
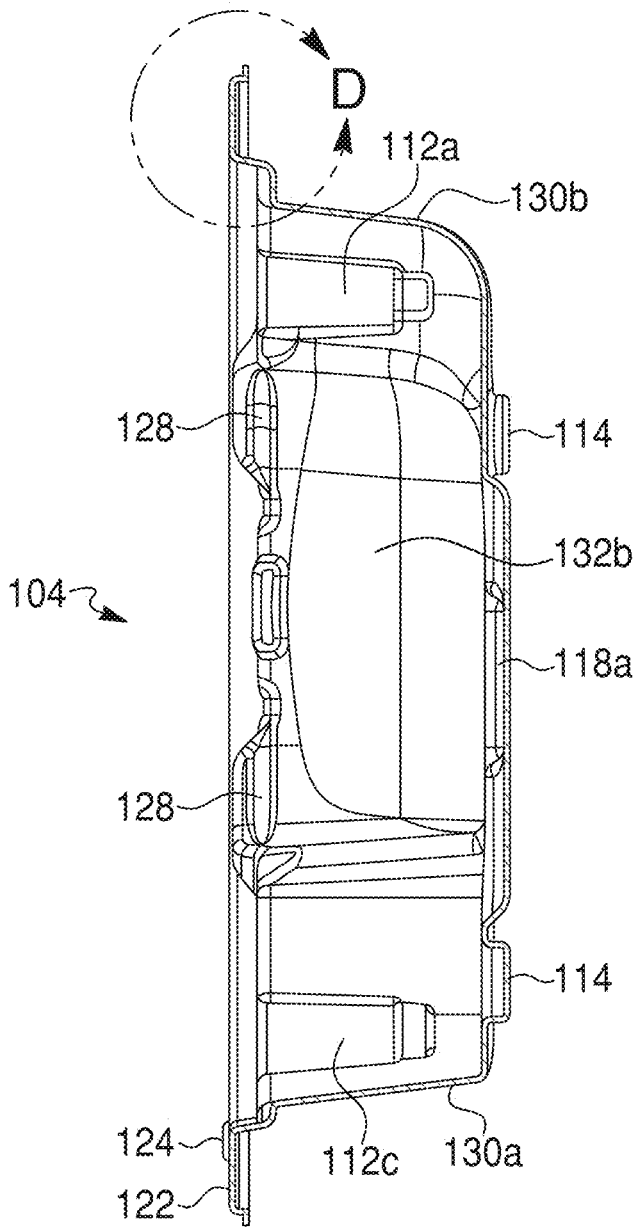

Tray 104 may include a plurality of lugs 112a, 112b, 112c, 112d. As shown in FIGS. 2 and 3A, lugs 112a, 112b, 112c, 112d may be shaped to correspond to the shape of device 102, as shown in FIG. 1. In some examples, lugs 112a, 112b, 112c, 112d may be shaped to form a space or gap between a portion of device 102 and tray 104. For example, once a user opens packaging 100 to expose device 102 within tray 104, a user may insert one or more fingers into the space and/or spaces formed by lugs 112a, 112b, 112c, 112d in order to grasp and/or lift device 102 from tray 104. Tray 104 may include at least two lugs, at least three lugs, or at least four lugs. FIGS. 3A and 3I depict lugs 112a, 112b, 112c, 112d in various positions. For example, FIG. 3A depicts a plurality of lugs 112a, 112b, 112c, 112d in offset positions where lug 112a is offset, i.e., not directly across from, lug 112b, and lug 112c is offset from lug 112d. In FIG. 3I, lug 112a is located across from lug 112b and lug 112c is located across from lug 112d. Referring to FIGS. 2 and 3A, first sidewall 130a of first plurality of sidewalls 130a, 130b may include lug 112a and 112c, second sidewall 130a of first plurality of sidewalls 130a, 130b may include lug 112d, and first sidewall 132a of second plurality of sidewalls 132a, 132b may include lug 112b. Referring to FIG. 3I, lug 112a and lug 112c may be located in a first sidewall 130a of first plurality of sidewalls 130a, 130b may include lug 112a and lug 112c and second sidewall 130b of first plurality of sidewalls 130a, 130b may include lug 112b and 112d. Lugs 112a, 112b, 112c, 112d may be positioned in any appropriate location to allow for a user to comfortably and/or easily grasp a portion of device 102 and/or lift device 102 from tray 104. Lugs 112a, 112b, 112c, 112d may also provide structural stability to tray 104 and/or additional space for the sterilant to circulate within tray 104 and/or around medical device 102. In other embodiments, lug 112a, 112b, 112c, 112d may aid in the manufacturing process of tray 104.

In some embodiments, tray 104 may include at least one indent 114. Indent 114 may be shaped to correspond to a portion of device 102. Indent 114 may have a generally circular or round shape. As shown in FIG. 3A, tray 104 may include a plurality of indents 114, for example, at least one indent 114, at least two indents 114, or at least three indents 114. Indent 114 may be placed at any appropriate location of tray 104 such that indent 114 properly fits against and/or corresponds to a portion of device 102. FIG. 3G depicts an exterior side view of tray 104 wherein each indent 114 projects outwards from the base of tray 104 away from cavity 108 and device 102 when device 102 is received in tray 104. In some embodiments, indent 114 may aid in the manufacturing process of tray 104, e.g., indent 114 may serve as an ejection surface from a mold.

In some embodiments, tray 104 may include a depression 118a, 118b, 118c on a bottom portion of tray 104. Depression 118a, 118b, 118c may be shaped to correspond to a portion of device 102, e.g., a drop pin of an auto-injector, which may also be referred to as an anti-firing mechanism. As shown in FIG. 3A, one of the depressions, e.g., depression 118a, may have a generally oval shape. In some embodiments, as shown in FIG. 3A, depression 118b may be located on one side of depression 118a and depression 118c may be located on an opposite side of depression 118a. In some embodiments, depression 118a, 118b, 118c may be flexible and may be configured to facilitate removal of device 102 from tray 104. Depression 118a, 118b, 118c may be associated with the base of tray 104 so that projection 116 is oriented beneath a device when device 102 is housed within tray 104 and packaging 100. Depression 118a, 118b, 118c may be made of a compressible material that deforms under pressure, e.g., pressure applied by a user. Depression 118a, 118b, 118c may be made of the same material as the rest of tray 104 or may be formed of a different material, e.g., a relatively more flexible material. In some embodiments, as discussed above, depression 118a, 118b, 118c and tray 104 may be thermoformed plastic. For example, depression 118a, 118b, 118c and/or tray 104 may be formed of one or more of polypropylene, polystyrene, polyethylene, polycarbonate, polyvinyl chloride, or polyethylene terephthalate glycol (PETG).

In some embodiments, packaging 100 may be configured for an auto-injector including a button or switch on a bottom surface of the auto-injector. In such embodiments, tray 104 may be configured such that the auto-injector securely fits into a portion of tray 104, e.g., at least one depression 118a, 118b, 118c, in order to prevent the button or switch from turning on, e.g., due to movement of the auto-injector within tray 104.

In some embodiments, tray 104 may include at least one groove 128. Groove 128 may be located on a sidewall of tray 104. As shown in FIG. 2, cavity 108 may include at least two grooves 128, at least three grooves 128, or at least four grooves 128. Referring to FIGS. 2 and 3A-3C, first sidewall 130a of first plurality of sidewalls 130a, 130b may include at least one groove 128. In other embodiments, second sidewall 130b of first plurality of sidewalls 132a, 132b may include at least one groove 128. In other examples, first sidewall 130a of first plurality of sidewalls 130a, 130b may include at least two grooves 128 and sidewall 130b of first plurality of sidewalls 130a, 130b may include at least two grooves 128. In other embodiments, one or more sidewalls 132a, 132b of second plurality of sidewalls 132a, 132b, may include groove 128. Each groove 128 may have a suitable shape such that device 102 may properly and securely fit into tray 104. As shown in FIGS. 2 and 3A, groove 128 may have a slightly curved shaped. Each groove 128 may be configured to correspond to a portion of retainer 106, which will be discussed in further detail. Each groove 128 may correspond to a portion of retainer 106 to form a snap fit or a friction fit such that retainer 106 may be secured to tray 104 to for packaging 100 for device 102.

As shown in FIG. 2, tray 104 may include at least one nub 134. Nub 134 may be located on one or more sidewalls 130a, 130b of first plurality of sidewalls 130a, 130b. Referring to FIG. 2, at least one nub 134 is located on sidewall 130a and at least one nub 134 is located on sidewall 130b. As shown in FIG. 2, nub 134 may have a generally rectangular shape. Nub 134 may have any appropriate shape and/or configuration in order to secure a portion of medical device 102 within tray 104. For example, nub 134 may form a snap fit with a portion of medical device 102 when medical device 102 is inserted into tray 104.

Referring back to FIGS. 2 and 3A, tray 104 may include a lip 110 extending around at least a portion of tray 104. Lip 110 may be configured to attach to a portion of retainer 106 and/or a portion of removable cover 107 to form a seal to enclose device 102 within packaging 100. In other embodiments, lip 110 may allow for removable, e.g., peelable, cover 107 to be sealed over the top opening of tray 104 to contain device 102 within tray 104 during storage and/or sterilization. An adhesive, e.g., a glue, paste, film, tape, pressure-sensitive material, and/or cold adhesive may be used to seal lip 110 to a portion of retainer 106 and/or to seal a portion of removable cover 107 to lip 110. The adhesive may be compatible for use with the type of external sterilization that may be performed on packaging 100 and/or the sterilant that may be included within packaging 100.

A corner of tray 104, e.g., corner 122 in FIG. 3A, may be free of an adhesive to allow a user to separate a removable cover 107 from tray 104. For example, corner 122 may be free of an adhesive to allow a user to lift a portion of removable cover 107 off of corner 122 in order to remove removable cover 107 from tray 104. As shown in FIGS. 3A, 3B, and 3F, corner 122 may include a tab 124 (or other projection or indentation) to allow a user to separate removable cover 107 from tray 104. For example, tab 124 may be configured such that a user may lift a portion of removable cover off of corner 122 in order to remove removable cover 107 from tray 104. Tab 124 may be correspond to a portion of, e.g., a corner of, removable cover 107, which will be discussed in further detail.

FIG. 3B depicts a cross-section view corresponding to section A-A of FIG. 3A. In some embodiments, a length of tray 104 may range from about 4 inches to about 7 inches. For example, a length of tray 104 may range from about 4 inches to about 6.5 inches, about 4 inches to about 6 inches, about 4 inches to about 5.5 inches, about 4.5 inches to about 7 inches, about 4.5 inches to about 6.5 inches, about 4.5 inches to about 6 inches, about 4.5 inches to about 5.5 inches, about 5 inches to about 7 inches, about 5 inches to about 6.5 inches, or about 5 inches to about 6 inches. In some examples, a length of tray 104 may range from about 4.5 inches to about 6.3 inches, about 4.5 inches to about 6.1 inches, about 4.5 inches to about 5.9 inches, about 4.5 inches to about 5.7 inches, about 4.5 inches to about 5.5 inches, about 4.5 inches to about 5.4 inches, about 4.7 inches to about 5.4 inches, about 4.9 inches to about 5.4 inches, about 5.1 inches to about 5.4 inches. In some examples, a length of tray 104 may be about 5 inches, about 5.1 inches, about 5.2 inches, about 5.3 inches, about 5.4 inches, about 5.5 inches, about 5.6 inches, about 5.7 inches, about 5.8 inches, or about 5.9 inches.

Referring to FIG. 3A, each edge of tray 104 may have a radius of curvature R ranging from about 30 R to 50 R. For example, the radius of curvature R may range from about 30 R to about 45 R, about 35 R to about 45 R, about 35 R to about 50 R, about 40 R to about 45 R, about 40 R to about 50 R, about 42 R to about 50 R, about 42 R to about 48 R, or about 42 R to about 46 R. In some examples, the radius of curvature R may be about 30 R, 31, R, 32, R, 33 R, 34 R, 35 R, 36 R, 37 R, 38 R, 39 R, 40 R, 41 R, 42 R, 43 R, 44 R, 45 R, 46 R, 47 R, 48 R, 49 R, or 50 R.

Figure 3C:
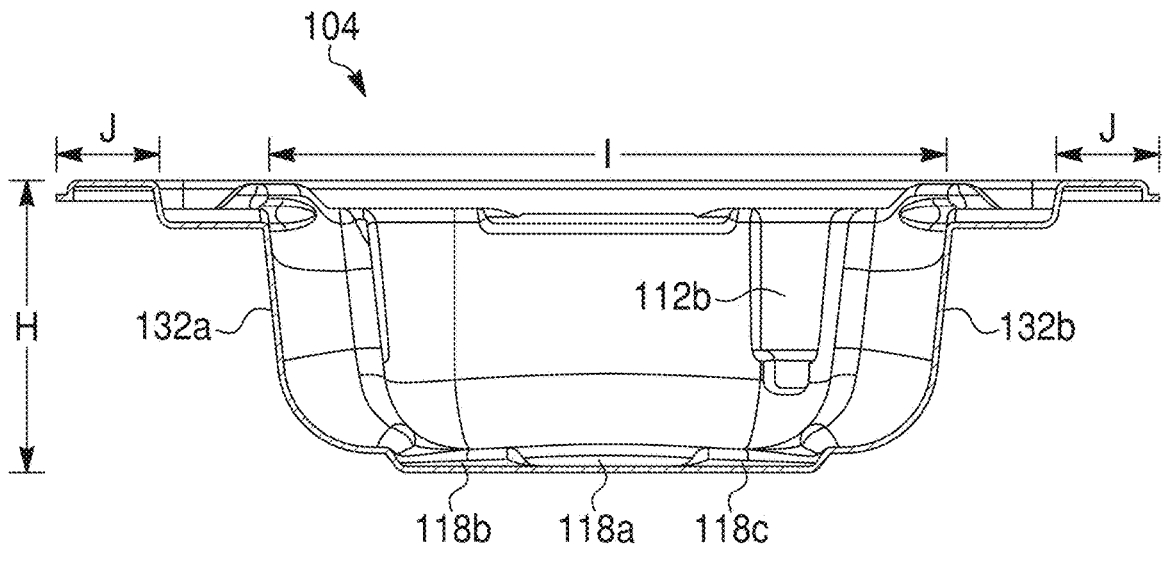

FIG. 3C depicts a cross-section view corresponding to section B-B of FIG. 3A. In some embodiments, a width of tray 104 may range from about 3 inches to about 6 inches. For example, a width of tray 104 may range from about 3 inches to about 5.5 inches, about 3 inches to about 5 inches, about 3.5 inches to about 6 inches, about 3.5 inches to about 5.5 inches, about 3.5 inches to about 5 inches, about 4 inches to about 6 inches, about 4 inches to about 5.5 inches, about 4 inches to about 5 inches, about 4.5 inches to about 6 inches, about 4.5 inches to about 5.5 inches, about 4.5 inches to about 5 inches. In some examples, a width of tray 104 may be about 4 inches, about 4.1 inches, about 4.2 inches, about 4.3 inches, about 4.4 inches, about 4.5 inches, about 4.6 inches, about 4.7 inches, about 4.8 inches, or about 4.9 inches.

Referring to FIG. 3C, a height H of tray 104 may range from about 1 inch to about 2 inches. For example, a height H of tray 104 may range from about 1 inch to about 1.9 inches, about 1 inch to about 1.8 inches, about 1 inch to about 1.7 inches, about 1 inch to about 1.6 inches, about 1 inch to about 1.5 inches, about 1 inch to about 1.4 inches, about 1 inch to about 1.3 inches, about 1.1 inches to about 2 inches, about 1.2 inches to about 2 inches, about 1.1 inches to about 1.9 inches, about 1.1 inches to about 1.8 inches, about 1.1 inches to about 1.7 inches, about 1.1 inches to about 1.6 inches, about 1.1 inches to about 1.5 inches, about 1.1 inches to about 1.4 inches, about 1.2 inches to about 2 inches, about 1.2 inches to about 1.9 inches, about 1.2 inches to about 1.8 inches, about 1.2 inches to about 1.7 inches, about 1.2 inches to about 1.6 inches, about 1.2 inches to about 1.5 inches, or about 1.2 inches to about 1.4 inches.

As shown in FIG. 3C, a width I of cavity 108 may range from about 2 inches to about 4 inches. For example, a width I of cavity may range from about 2 inches to about 3.9 inches, about 2 inches to about 3.8 inches, about 2 inches to about 3.7 inches, about 2 inches to about 3.6 inches, about 2 inches to about 3.5 inches, about 2 inches to about 3.4 inches, about 2 inches to about 3.3 inches, about 2 inches to about 3.2 inches, about 2 inches to about 3.1 inches, about 2 inches to about 3 inches, about 2.1 inches to about 3 inches, about 2.2 inches to about 3 inches, about 2.3 inches to about 3 inches, about 2.4 inches to about 3 inches, about 2.5 inches to about 3 inches, about 2.6 inches to about 3 inches, about 2.7 inches to about 3 inches, about 2.8 inches to about 3 inches, about 2.9 inches to about 3 inches, about 2.5 inches to about 4 inches, about 2.6 inches to about 4 inches, about 2.7 inches to about 4 inches, about 2.8 inches to about 4 inches, or about 2.9 inches to about 4 inches.

Also referring to FIG. 3C, a width J of lip 110 may range from about 0.1 inch to about 0.5 inch. For example, a width J of lip 110 may range from about 0.1 inch to about 0.45 inch, about 0.1 inch to about 0.4 inch, about 0.1 inch to about 0.35 inch, about 0.15 inch to about 0.5 inch, about 0.15 inch to about 0.45 inch, about 0.15 inch to about 0.4 inch, about 0.15 inch to about 0.3 inch, about 0.2 inch to about 0.5 inch, about 0.2 inch to about 0.45 inch, about 0.2 inch to about 0.4 inch, about 0.2 inch to about 0.35 inch, about 0.2 inch to about 0.3 inch, about 0.25 inch to about 0.3 inch, about 0.25 inch to about 0.35 inch, about 0.25 inch to about 0.4 inch, about 0.25 inch to about 0.5 inch.

Figure 3D:
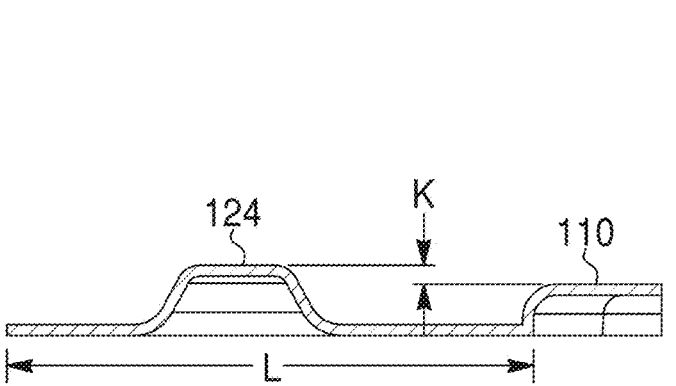

FIG. 3D depicts a cross-section view corresponding to section C-C of FIG. 3A. As shown in FIG. 3D, a portion of tab 124 may extend above lip 110 at a distance K ranging from about 0.01 inch to about 0.5 inch. For example, distance K may range from about 0.01 inch to about 0.4 inch, about 0.01 inch to about 0.3 inch, about 0.01 inch to about 0.2 inch, about 0.01 inch to about 0.1 inch, about 0.01 inch to about 0.09 inch, about 0.01 inch to about 0.08 inch, about 0.01 inch to about 0.07 inch, about 0.01 inch to about 0.06 inch, about 0.01 inch to about 0.05 inch, about 0.01 to about 0.04 inch, about 0.02 inch to about 0.5 inch, about 0.02 inch to about 0.4 inch, about 0.02 inch to about 0.3 inch, about 0.02 inch to about 0.2 inch, about 0.02 inch to about 0.1 inch, about 0.02 inch to about 0.09 inch, about 0.02 inch to about 0.08 inch about 0.02 inch to about 0.07 inch, about 0.02 inch to about 0.06 inch, about 0.02 inch to about 0.05 inch, or about 0.02 inch to about 0.04 inch.

Also referring to FIG. 3D, the outer edge of corner 122 to the outer edge of lip 110 corresponds to distance L. Distance L may range from about 0.5 inch to about 1.5 inches. For example, distance L may range from about 0.5 inch to about 1.4 inches, about 0.5 inch to about 1.3 inches, about 0.5 inch to about 1.2 inches, about 0.5 inch to about 1.1 inches, about 0.5 inch to about 1 inch, about 0.5 inch to about 0.9 inch, about 0.6 inch to about 1.5 inches, about 0.6 inch to about 1.4 inches, about 0.6 inch to about 1.3 inches, about 0.6 inch to about 1.2 inches, about 0.6 inch to about 1.1 inches, about 0.6 inch to about 1 inch, about 0.6 inch to about 0.9 inch, about 0.7 inch to about 1.5 inches, about 0.7 inch to about 1.4 inches, about 0.7 inch to about 1.3 inches, about 0.7 inch to about 1.2 inches, about 0.7 inch to about 1.1 inches, about 0.7 inch to about 1 inch, about 0.7 inch to about 0.9 inch, about 0.8 inch to about 1.5 inches, about 0.8 inch to about 1.4 inches, about 0.8 inch to about 1.3 inches, about 0.8 inch to about 1.2 inches, about 0.8 inch to about 1.1 inches, or about 0.8 inch to about 1 inch.

Figure 3E:
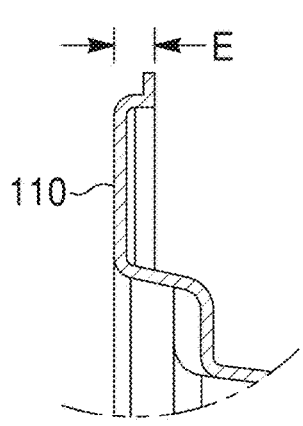
Figure 3F:
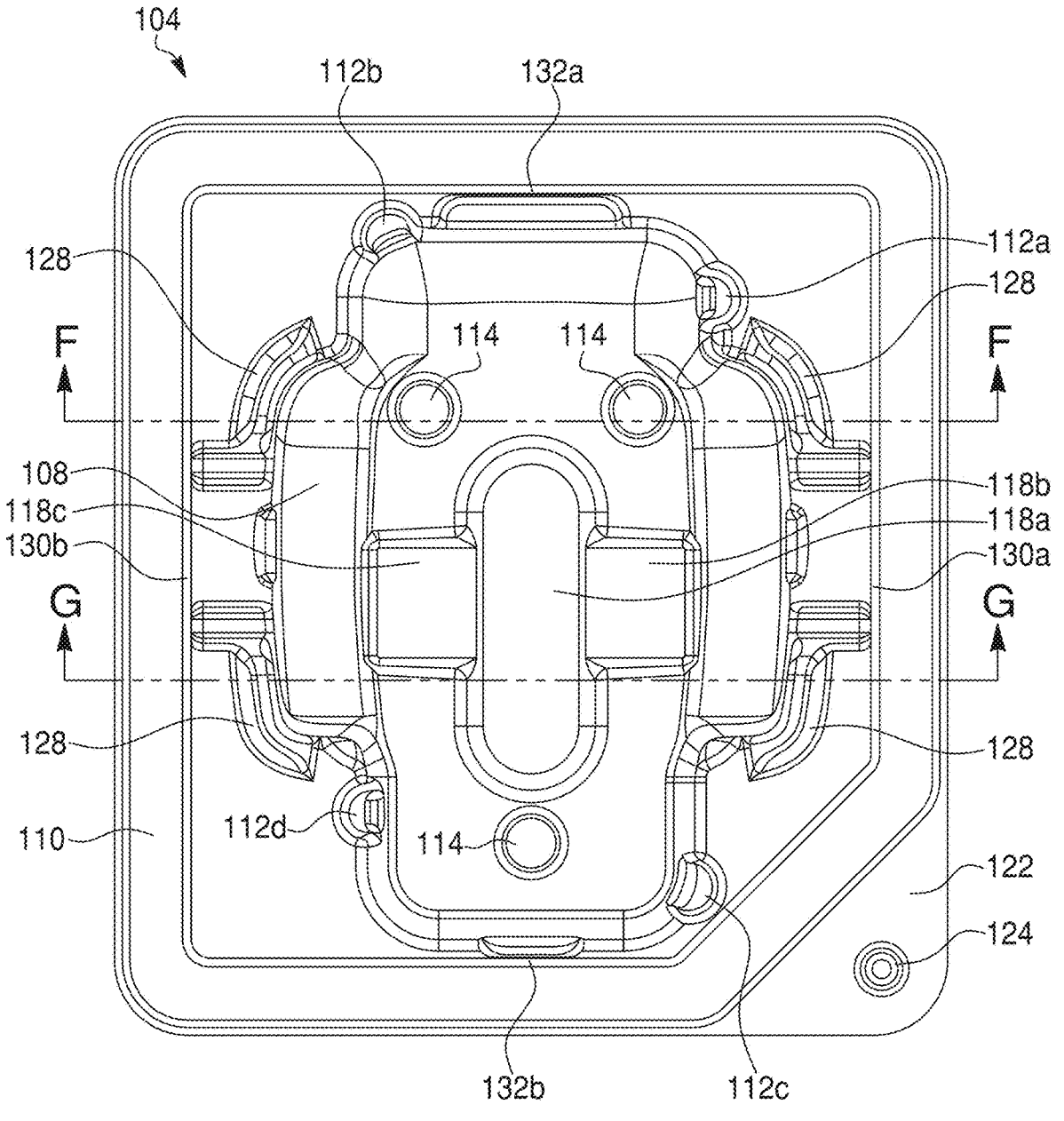
Figure 3G:
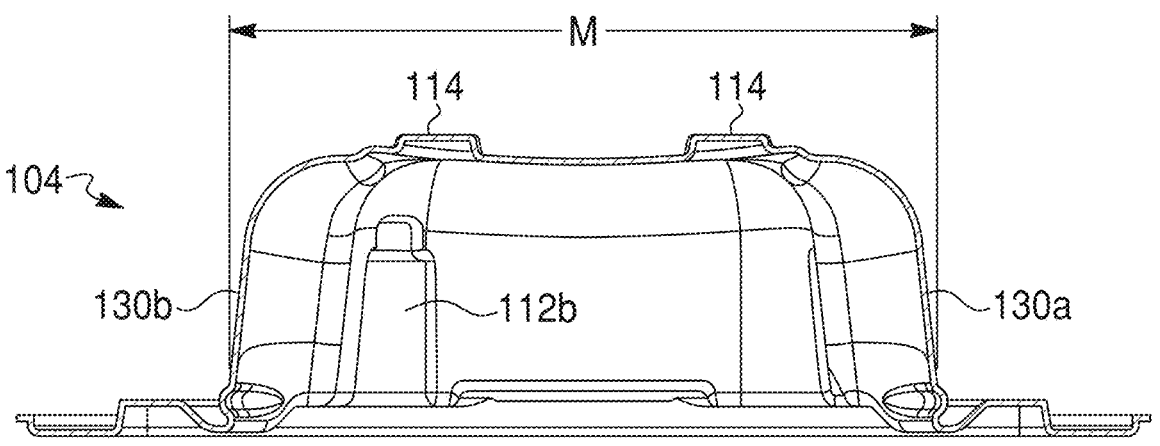

FIG. 3E depicts an enlarged view of detail D of FIG. 3B. As shown in FIG. 3E, a height E of lip 110 on an outer edge of tray 104 may range from about 0.05 inch to 0.5 inch. For example, a height E of lip 110 may range from about 0.05 inch to about 0.4 inch, about 0.05 inch to about 0.3 inch, about 0.05 inch to about 0.2 inch, about 0.05 inch to about 0.1 inch, about 0.06 inch to about 0.5 inch, about 0.06 inch to about 0.4 inch, about 0.06 inch to about 0.3 inch, about 0.06 inch to about 0.2 inch, about 0.06 inch to about 0.1 inch, about 0.07 inch to about 0.5 inch, about 0.07 inch to about 0.4 inch, about 0.07 inch to about 0.3 inch, about 0.07 inch to about 0.2 inch, about 0.07 inch to about 0.1 inch, or about 0.07 inch to about 0.09 inch.

Figure 3H:
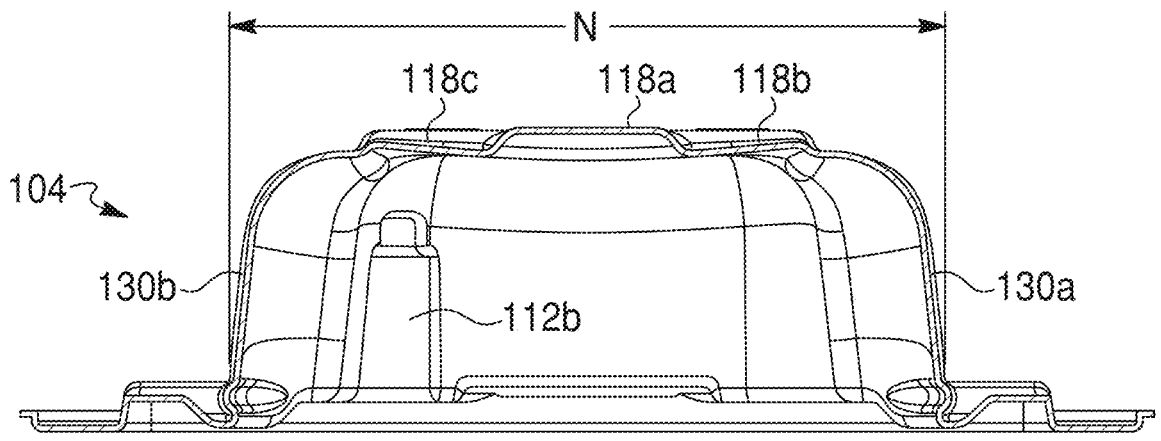
Figure 3I:
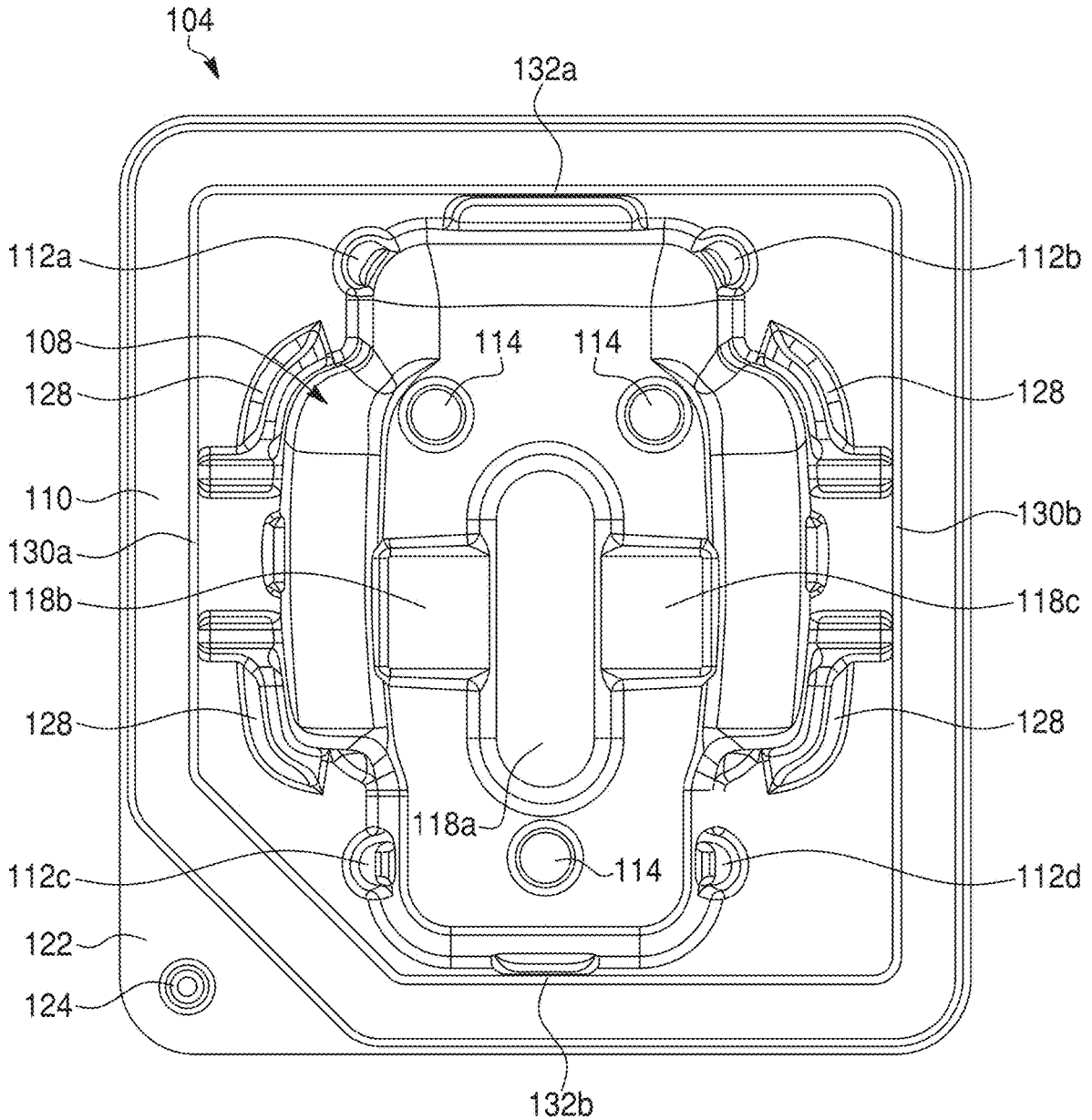
FIG. 3I provides a top view of an exemplary tray, according to an embodiment of the present disclosure.

FIG. 3F depicts a bottom view of tray 104. FIG. 3G depicts a cross-section view corresponding to section F-F of FIG. 3F and FIG. 3H depicts a cross-section view corresponding to section G-G of FIG. 3F. A width M of the external surface of cavity 108, as depicted in FIG. 3G, may range from about 3 inches to about 4 inches. For example, width M may range from about 3 inches to about 3.9 inches, about 3 inches to about 3.8 inches, about 3 inches to about 3.7 inches, about 3 inches to about 3.6 inches, about 3 inches to about 3.5 inches, about 3 inches to about 3.4 inches, about 3 inches to about 3.3 inches, or about 3 inches to about 3.2 inches. A width N of the external surface of cavity 108, as depicted in FIG. 3H, may range from about 3 inches to about 4 inches. For example, width N may range from about 3 inches to about 3.9 inches, about 3 inches to about 3.8 inches, about 3 inches to about 3.7 inches, about 3 inches to about 3.6 inches, about 3 inches to about 3.5 inches, about 3 inches to about 3.4 inches, about 3 inches to about 3.3 inches, or about 3 inches to about 3.2 inches.

Figure 4:
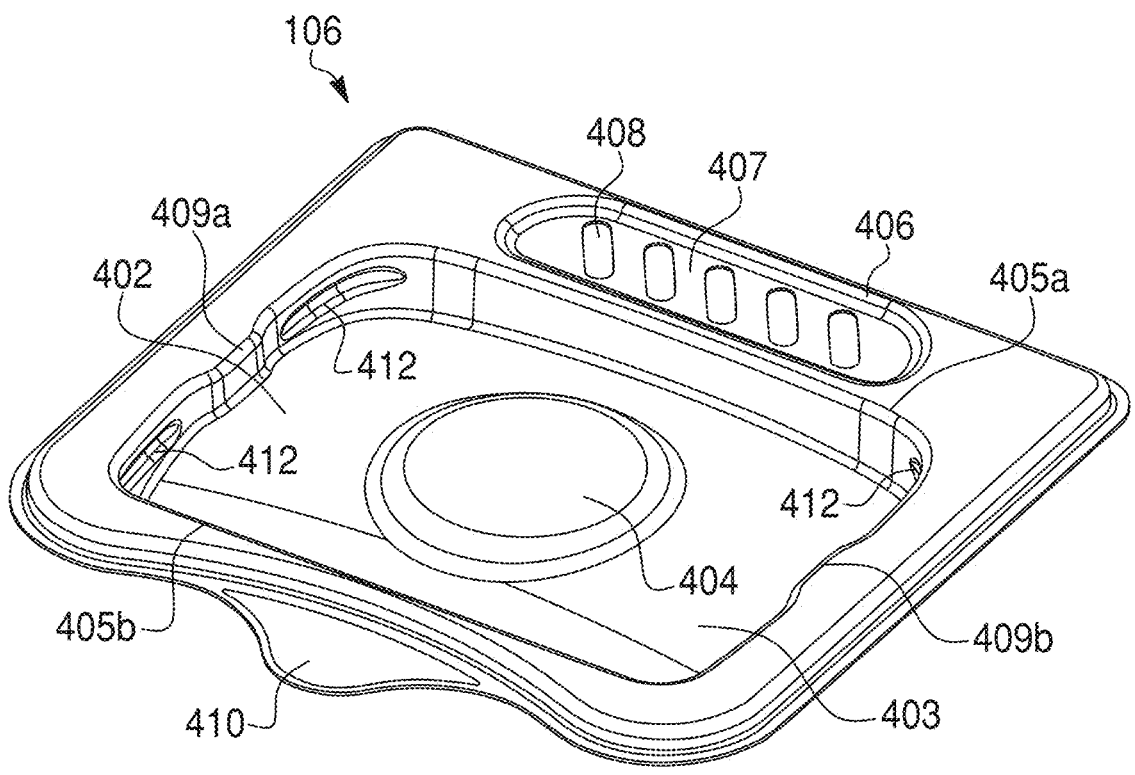
FIG. 4 provides a perspective view of an exemplary retainer, according to an embodiment of the present disclosure.
Figure 5A:
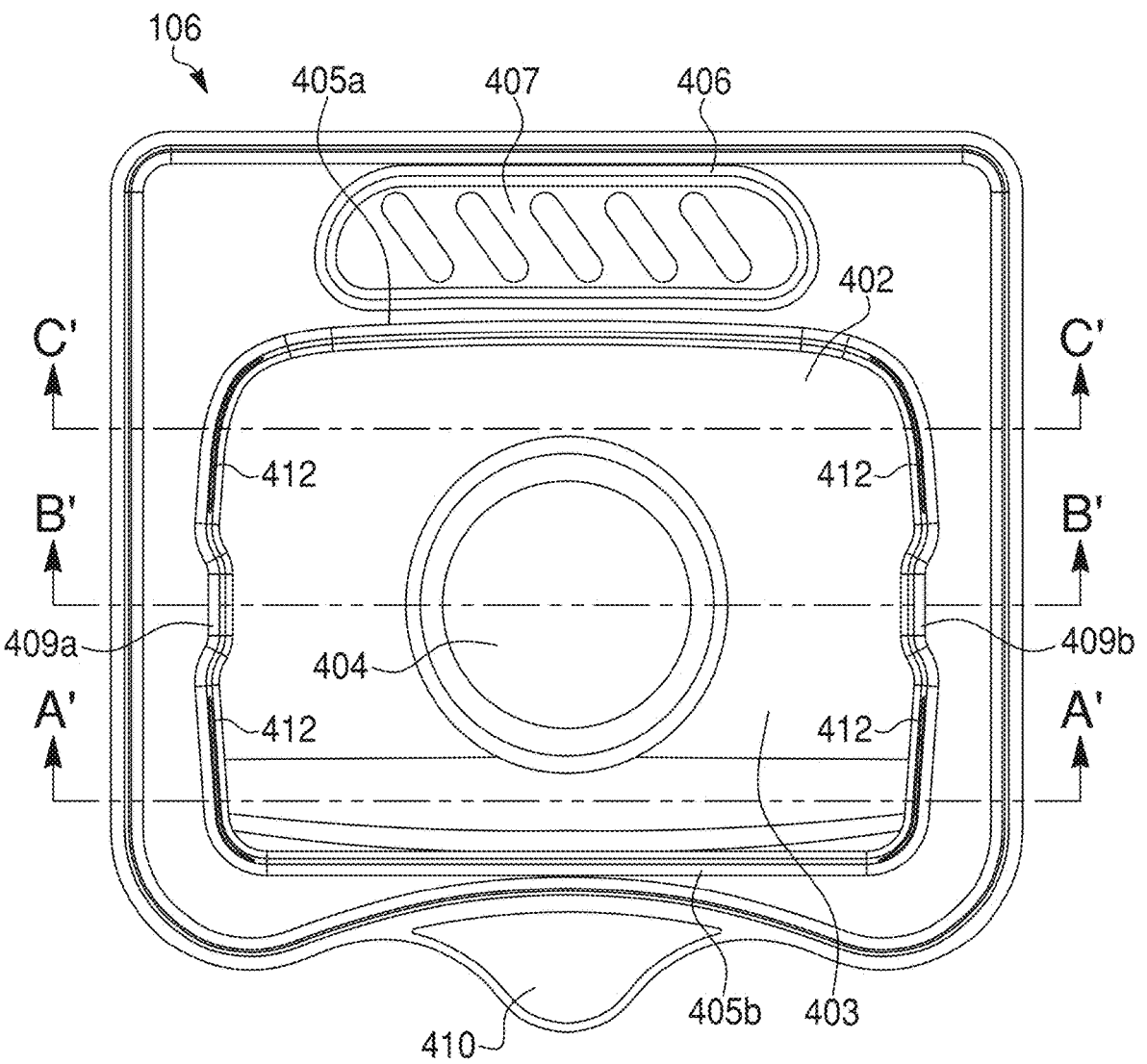
FIGS. 5A-5E provide detailed views of an exemplary retainer, according to an embodiment of the present disclosure.
Figure 5B:
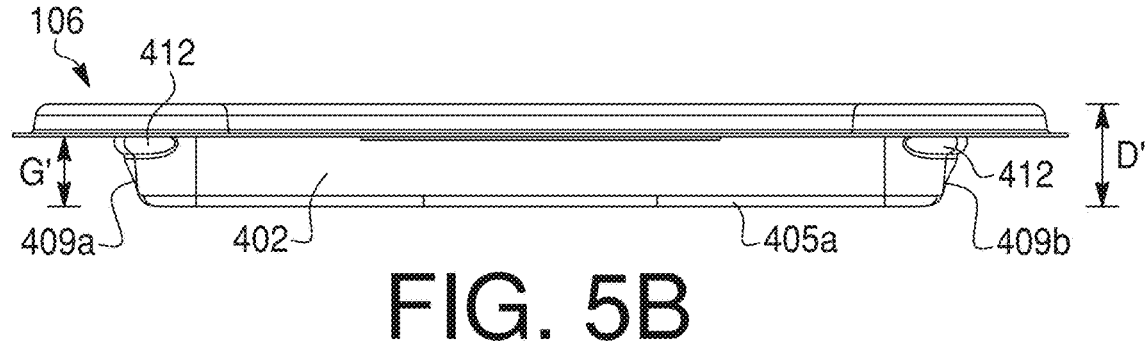
Figure 5C:
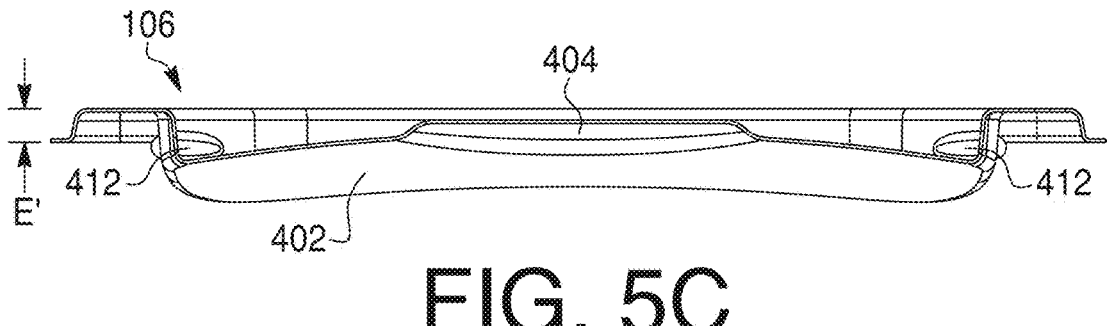
Figure 5D:
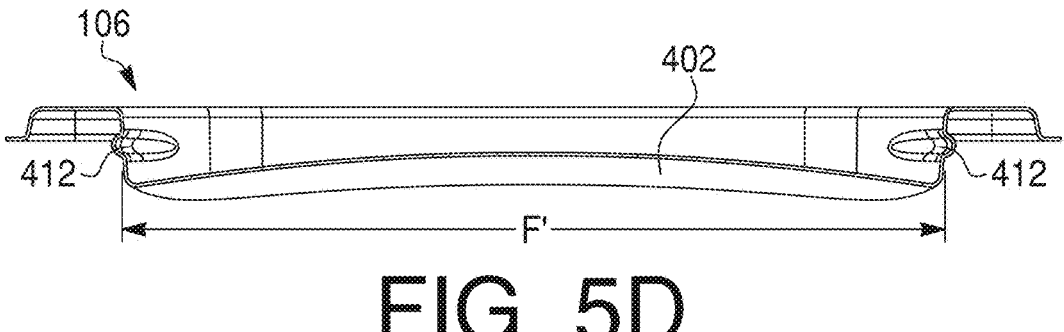
Figure 5E:
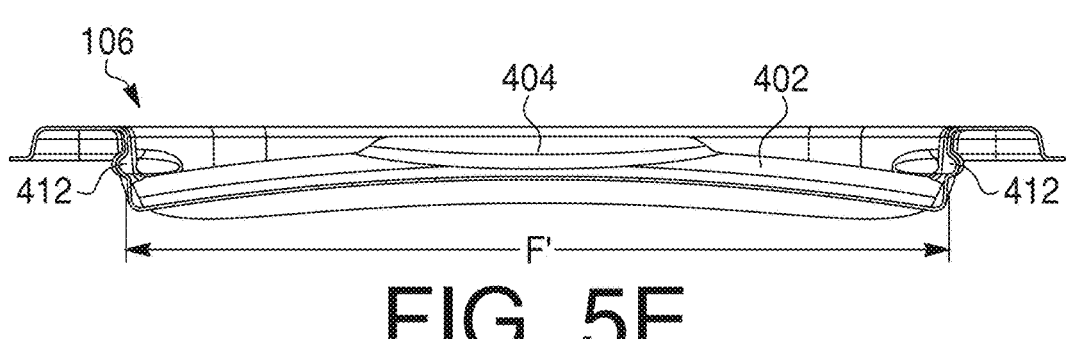

FIGS. 4-5E depict an exemplary retainer 106 of packaging 100. Referring to FIG. 4, retainer 106 may include a plurality of cavities 402, 406. Retainer 106 may have a first cavity 402 and a second cavity 406. In other embodiments, retainer 106 may include at least two cavities, at least three cavities, or at least four cavities. As shown in FIG. 4, first cavity 402 may include a base 403, a first plurality of sidewalls 405a, 405b, and a second plurality of sidewalls 409a, 409b. In some embodiments, a length of first plurality of sidewalls 405a, 405b may be larger than a length of second plurality of sidewalls 409a, 409b. In other embodiments, a length of first plurality of sidewalls 405a, 405b may be less than a length of second plurality of sidewalls 409a, 409b. In other embodiments, a length of first plurality of sidewalls 405a, 405b may be equal to a length of second plurality of sidewalls 409a, 409b. In other embodiments, second cavity 406 may include a base 407.

As shown in FIG. 4, retainer 106 may include a dome 404 and a plurality of apertures 412. In some embodiments, base 403 of retainer 106 may include dome 404. Dome 404 may have a suitable shape such that dome 404 abuts to and/or forms a friction fit with a portion of device 102, e.g., as shown in FIG. 1, when retainer 106 is attached to tray 104 to form packaging 100. Dome 404 may protect a portion of device 102, e.g., an upper portion of device 102, and/or interface with a portion of device 102. In some embodiments, dome 404 may contain a sterilant as discussed above.

Referring to FIGS. 4 and 5A, retainer 106 may include at least two apertures 412, at least three apertures 412, or at least four apertures 412. Each aperture 412 may have a suitable shape such that when device 102 is placed into cavity 108 of tray 104 and retainer 106 is sealed to a portion of tray 104, retainer 106 may securely and properly fit with and/or seal with tray 104 and each aperture 412 may fit into a corresponding groove 128 of tray 104, as shown in FIGS. 2 and 3A. As shown in FIG. 4, aperture 412 may have a slightly curved shape. Each aperture 412 may be configured to correspond to the shape of corresponding groove 128 to form a friction fit such that retainer 106 may be secured to tray 104 for packaging 100 for device 102. Each aperture 412 may also be placed at a location of first cavity 402 such that each aperture 412 properly secures to and/or is received in corresponding groove 128. For example, each sidewall of first plurality of sidewalls 405a, 405b may include a portion of aperture 412. In other embodiments, each sidewall of second plurality of sidewalls 409a, 409b may include a portion of aperture 412. As shown in FIGS. 4 and 5A, aperture 412 may have a slightly curved shaped such that at least one aperture 412 may extend from a portion of sidewall 405a to a portion of sidewall 409a, at least one aperture 412 may extend from a portion of sidewall 405a to a portion of sidewall 409b, at least one aperture 412 may extend from a portion of sidewall 405b to a portion of sidewall 409a, and at least one aperture 412 may extend from a portion of sidewall 405b to a portion of sidewall 409b.

Second cavity 406 of retainer 106 may include a base 407. In some embodiments, base 407 may include at least one vent 408. When retainer 106 is secured to tray 104 to enclose device 102, vent 408 may allow for airflow into tray 104 and/or around device 102. Vent 408 may also allow for sterilization and/or for any sterilant contained in packaging 100, e.g., in tray 104, to flow within packaging 100. Vent 408 may encourage the flow of and/or increase the penetration of sterilant gas into packaging 100 and its components. Base 407 of second cavity 406 may include a plurality of vents 408, e.g., at least one vent 408, at least two vents 408, at least three vents 408, at least four vents 408, or at least five vents, etc. As shown in FIG. 4, first cavity 402 has a generally square shape and second cavity 406 has a generally rectangular shape. First cavity 402 and second cavity 406 may have any appropriate shape or configuration that allows retainer 106 to properly secure to, abut against, and/or form a friction fit with, tray 104. Retainer 106 may also include an overhang 410 for assisting a user in separating retainer 106 from tray 104, e.g., the removal of retainer 106 from tray 104. Overhang 410 may have any appropriate shape allowing retainer 106 to properly secure to, abut against, and/or form a friction fit with, tray 104, and allowing for a user to properly separate retainer 106 from tray 104. During use, after a user removes removable cover 107 from tray 104, a user may grasp a portion of overhang 410 and lift a portion of overhang 410 in an upwards motion to separate retainer 106 from tray 104. The user may then remove the device from tray 104.

Retainer 106 may be made of a compressible material that deforms under pressure, e.g., pressure applied by a user. In some embodiments, retainer 106 may be thermoformed plastic. For example, retainer 106 may be formed of one or more of polypropylene, polystyrene, polyethylene, polycarbonate, polyvinyl chloride, polyethylene terephthalate glycol (PETG).

Referring to FIG. 5A, a length of retainer 106 extending from a top edge of retainer 106 to a bottom edge of overhang 410 may range from about 3 inches to about 4 inches. For example, a length of retainer 106 may range from about 3 inches to about 3.9 inches, about 3 inches to about 3.8 inches, about 3.1 inches to about 4 inches, about 3.2 inches to about 4 inches, about 3.3 inches to about 4 inches, about 3.4 inches to about 4 inches, about 3.5 inches to about 4 inches, about 3.6 inches to about 4 inches, about 3.7 inches to about 4 inches, about 3.7 inches to about 3.8 inches, about 3.7 inches to about 3.9 inches, about 3.6 inches to about 3.8 inches, about 3.6 inches to about 3.9 inches, about 3.5 inches to about 3.8 inches, or about 3.5 inches to about 3.9 inches.

A width of retainer 106 may range from about 3 inches to about 4 inches. For example, a width of retainer 106 may range from about 3.1 inches to about 4 inches, about 3.2 inches to about 4 inches, about 3.3 inches to about 4 inches, about 3.4 inches to about 4 inches, about 3.5 inches to about 4 inches, about 3.6 inches to about 4 inches, about 3.7 inches to about 4 inches, about 3.8 inches to about 4 inches, about 3 inches to about 3.9 inches, about 3.1 inches to about 3.9 inches, about 3.2 inches to about 3.9 inches, about 3.3 inches to about 3.9 inches, about 3.4 inches to about 3.9 inches, about 3.5 inches to about 3.9 inches, about 3.6 inches to about 3.9 inches, about 3.7 inches to about 3.9 inches, or about 3.8 inches to about 3.9 inches.

FIG. 5B depicts a front view of retainer 106. A height D' of retainer 106 may range from about 0.2 inches to about 0.5 inches. For example, height D' of retainer 106 may range from about 0.2 inches to about 0.49 inches, about 0.2 inches to about 0.45 inches, about 0.2 inches to about 0.43 inches, about 0.2 inches to about 0.4 inches, about 0.23 inches to about 0.5 inches, about 0.25 inches to about 0.5 inches, about 0.27 inches to about 0.5 inches, about 0.3 inches to about 0.5 inches, about 0.33 inches to about 0.5 inches, about 0.35 inches to about 0.5 inches, about 0.3 inches to about 0.5 inches, about 0.45 inches, about 0.3 inches to about 0.43 inches, about 0.3 inches to about 0.4 inches, or about 0.35 inches to about 0.4 inches.

Referring to FIG. 5B, any one of first plurality of sidewalls 405a, 405b, second plurality of sidewalls 409a, 409b, and base 403 may extend away from a surface of retainer 106 such that when retainer 106 is secured to tray 104 to enclose device 102, at least a portion of base 403 abuts against a portion of device 102. A height G' of first cavity 402 may range from about 0.1 inches to about 0.4 inches. For example, height G' of first cavity 402 may range from about 0.15 inches to about 0.4 inches, about 0.18 inches to about 0.4 inches, about 0.2 inches to about 0.4 inches, about 0.22 inches to about 0.4 inches, about 0.1 inches to about 0.35 inches, about 0.1 inches to about 0.33 inches, about 0.1 inches to about 0.3 inches, about 0.1 inches to about 0.28 inches, about 0.15 inches to about 0.28 inches, about 0.15 inches to about 0.3 inches, about 0.15 inches to about 0.33 inches, about 0.15 inches to about 0.35 inches, about 0.18 inches to about 0.3 inches, about 0.18 inches to about 0.28 inches, about 0.2 inches to about 0.28 inches, about 0.2 inches to about 0.3 inches, about 0.22 inches to about 0.3 inches, about 0.22 inches to about 0.28 inches, about 0.22 inches to about 0.32 inches, about 0.2 inches to about 0.29 inches, or about 0.21 inches to about 0.29 inches.

FIG. 5C depicts a cross-section view corresponding to section B'-B' of FIG. 5A. Referring to FIG. 5C, a height E' of the portion of retainer 106 surrounding first cavity 402 may range from about 0.01 inches to about 0.25 inches. This portion of retainer 106 may be referred to as a ledge. For example, height E' of the ledge of retainer 106 may range from about 0.01 inches to about 0.22 inches, about 0.01 inches to about 0.2 inches, about 0.01 inches to about 0.18 inches, about 0.01 inches to about 0.16 inches, about 0.01 inches to about 0.14 inches, about 0.05 inches to about 0.25 inches, about 0.05 inches to about 0.22 inches, about 0.05 inches to about 0.2 inches, about 0.05 inches to about 0.18 inches, about 0.05 inches to about 0.15 inches, about 0.05 inches to about 0.13 inches, 0.08 inches to about 0.13 inches, about 0.1 inches to about 0.13 inches, about 0.1 inches to about 0.25 inches, about 0.1 inches to about 0.22 inches, about 0.1 inches to about 0.2 inches, about 0.1 inches to about 0.18 inches, or about 0.1 inches to about 0.15 inches.

FIG. 5D depicts a cross-section view corresponding to section C'-C' OF FIG. 5A and FIG. 5E depicts a cross-section view corresponding to section A'-A' of FIG. 5A. Referring to FIGS. 5D and 5E, a width F' of cavity 402 may range from about 2.5 inches to about 4.5 inches. For example, width F' of cavity 402 may range from about 2.6 inches to about 4.5 inches, about 2.7 inches to about 4.5 inches, about 2.8 inches to about 4.5 inches, about 2.9 inches to about 4.5 inches, about 3 inches to about 4.5 inches, about 3 inches to about 4.4 inches, about 3 inches to about 4.3 inches, about 3 inches to about 4.2 inches, about 3 inches to about 4.1 inches, about 3 inches to about 4 inches, about 3 inches to about 3.9 inches, about 3 inches to about 3.8 inches, about 3 inches to about 3.7 inches, about 3 inches to about 3.6 inches, about 3 inches to about 3.5 inches, about 3 inches to about 3.4 inches, about 3 inches to about 3.3 inches, about 3 inches to about 3.2 inches, about 3 inches to about 3.1 inches, about 2.9 inches to about 3.1 inches, or about 2.8 inches to about 3.1 inches.

Figure 6:
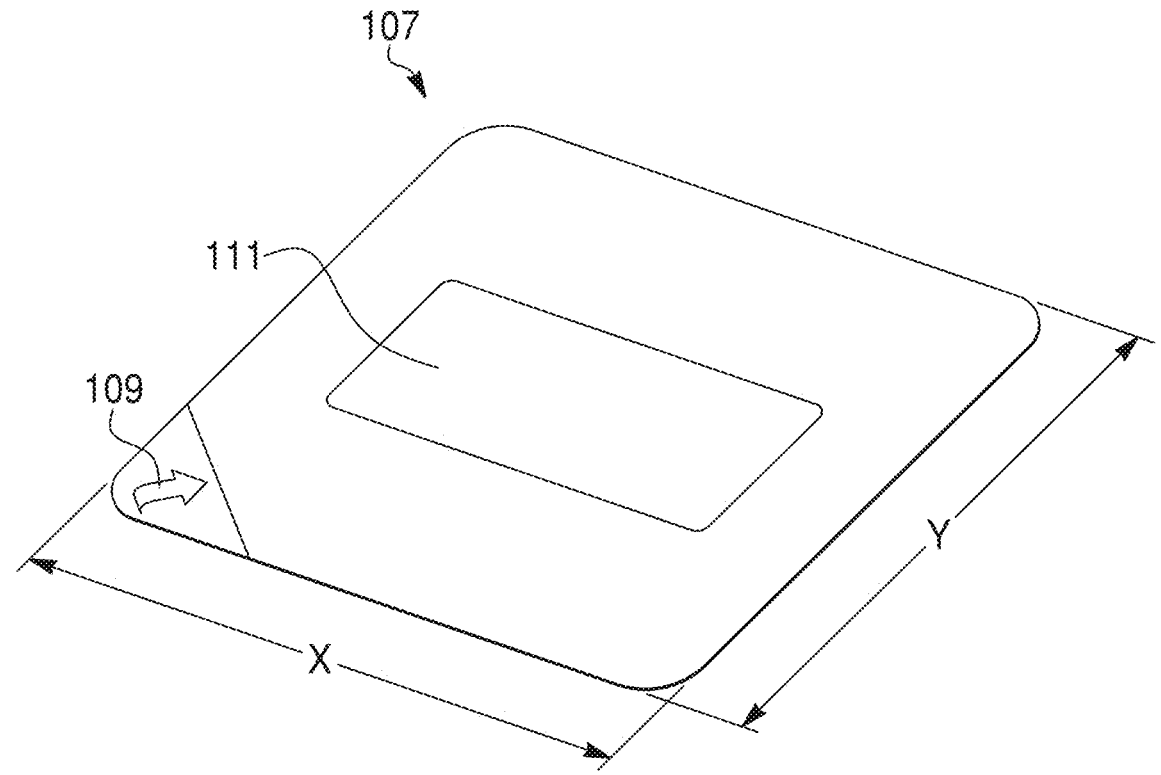
FIG. 6 provides a detailed view of an exemplary removable cover, according to an embodiment of the present disclosure.

FIG. 6 depicts removable cover 107. Removable cover 107 may be permeable to vapor hydrogen peroxide and/or an ethyl alcohol. Removable cover 107 may be formed of, e.g., Tyvek or other suitable high-density polyethylene fibers, ethylene-vinyl acetate, and/or other thermoplastic materials. Removable cover 107 may be permeable to a suitable gaseous sterilant, such as ethylene oxide, vaporized hydrogen peroxide, ethyl alcohol, nitrous oxide, nitrogen dioxide, or any appropriate sterilant in the art. As mentioned above, components of packaging 100, e.g., tray 104, retainer 106, and/or removable cover 107, and the size and/or shape of such components may be configured to facilitate high speed manufacturing of packaging 100 and/or improve material distribution of packaging 100.

As shown in FIG. 6, removable cover 107 may include a flap 109. Flap 109 may be configured such that a user may grasp a portion of flap 109 to lift a portion of removable cover 107 off of corner 122 and/or tab 124 of tray 104 in order to remove removable cover 107 from tray 104. Removable cover 107 may include an adhesive, e.g., a glue, paste, film, tape, pressure-sensitive material, and/or cold adhesive. For example, such adhesive may be applied to a portion of removable cover 107 that adheres to tray 104. The adhesive of removable cover 107 may be used to seal a portion of removable cover 107 to a portion of tray 104, e.g., lip 110 of tray 104. The adhesive may be compatible for use with the type of external sterilization that may be performed on packaging 100 and/or the sterilant that may be included within packaging 100. In some examples, flap 109 of removable cover 107 may be free of any adhesive. In packaging 100, removable cover 107 may not adhere to and/or secure any portion of medical device 102. Removable cover 107 is secured to a portion of tray 104 in order to form an enclosure for medical device 102 and/or retainer 106. Such enclosure formed by removable cover 107 and tray 104 allows for proper storage and/or sterilization of medical device 102.

Referring to FIG. 6, a length Y of removable cover 107 may range from about 4 inches to about 7 inches. For example, a length Y of removable cover 107 may range from about 4 inches to about 6.5 inches, about 4 inches to about 6 inches, about 4 inches to about 5.5 inches, about 4.5 inches to about 7 inches, about 4.5 inches to about 6.5 inches, about 4.5 inches to about 6 inches, about 4.5 inches to about 5.5 inches, about 5 inches to about 7 inches, about 5 inches to about 6.5 inches, or about 5 inches to about 6 inches. In some examples, a length Y of removable cover 7 may range from about 4.5 inches to about 6.3 inches, about 4.5 inches to about 6.1 inches, about 4.5 inches to about 5.9 inches, about 4.5 inches to about 5.7 inches, about 4.5 inches to about 5.5 inches, about 4.5 inches to about 5.4 inches, about 4.7 inches to about 5.4 inches, about 4.9 inches to about 5.4 inches, about 5.1 inches to about 5.4 inches. In some examples, a length Y of removable cover 107 may be about 5 inches, about 5.1 inches, about 5.2 inches, about 5.3 inches, about 5.4 inches, about 5.5 inches, about 5.6 inches, about 5.7 inches, about 5.8 inches, or about 5.9 inches.

Referring to FIG. 6, a width X of removable cover 107 may range from about 3 inches to about 6 inches. For example, a width X of removable cover 107 may range from about 3 inches to about 5.5 inches, about 3 inches to about 5 inches, about 3.5 inches to about 6 inches, about 3.5 inches to about 5.5 inches, about 3.5 inches to about 5 inches, about 4 inches to about 6 inches, about 4 inches to about 5.5 inches, about 4 inches to about 5 inches, about 4.5 inches to about 6 inches, about 4.5 inches to about 5.5 inches, about 4.5 inches to about 5 inches. In some examples, a width X of removable cover 107 may be about 4 inches, about 4.1 inches, about 4.2 inches, about 4.3 inches, about 4.4 inches, about 4.5 inches, about 4.6 inches, about 4.7 inches, about 4.8 inches, or about 4.9 inches.

Exemplary medicaments, drugs, and/or pharmaceutical formulations that may be used with the medical devices of the disclosure, e.g., auto-injectors, include: pharmaceuticals targeting Activin A and GDF8 (e.g., garetosmab and trevogrumab as described in U.S. Pat. No. 9,718,881, which is incorporated by reference herein); pharmaceuticals targeting C5 (e.g., pozelimab and cemdisiran, as described in US Publication 2021/0046182, which is incorporated by reference herein); pharmaceuticals targeting LEPR (e.g., mibavademab, as described in U.S. Pat. No. 10,023,644, which is incorporated by reference herein); pharmaceuticals targeting LAG3 (e.g., fianlimab, as described in U.S. Pat. No. 10,358,495, which is incorporated by reference herein); pharmaceuticals targeting BetV1 (e.g., antibodies disclosed in U.S. Pat. No. 10,793,624, which is incorporated by reference herein); pharmaceuticals targeting PCSK9 (e.g., alirocumab, as described in U.S. Pat. No. 8,795,669, which is incorporated by reference herein); pharmaceuticals targeting ANGPTL3 (e.g., evinacumab, as disclosed in US Publication 2020/0369760, which is incorporated by reference herein); pharmaceuticals targeting Ebola (e.g., atolivimab, maftivimab, odesivimab, as disclosed in US Publication 2021/0252146, which is incorporated by reference herein); pharmaceuticals targeting IL-6R (e.g., sarilumab, as disclosed in U.S. Pat. No. 9,173,880, which is incorporated by reference herein).

Additional exemplary medicaments, drugs, and/or pharmaceutical formulations include: RNAi therapeutic targeting APP for early-onset Alzheimer's disease (ALN-APP1); RNAi therapeutic targeting HSD17B13 for nonalcoholic steatohepatitis ("NASH") (ALN-HSD); RNAi therapeutic targeting PNPLA3 for NASH (ALN-PNP1); PD-1 Antibody for First-line NSCLC, BNT116 combination (CE-MIPLIMAB); Bispecific antibody targeting BCMA and CD3 for Multiple myeloma (LINVOSELTAMAB); TTR gene knockout using CRISPR/Cas9 for Transthyretin ("ATTR") amyloidosis; Bispecific antibody targeting CD20 and CD3 for certain B-cell malignancies (ODRONEX-TAMAB); Bispecific antibody targeting PSMA and CD3 for prostate cancer; Bispecific antibody targeting two distinct MET epitopes for MET-altered advanced NSCLC; Bispecific antibody-drug conjugate targeting two distinct MET epitopes for MET overexpressing advanced cancer; Agonist Antibody to NPR1/Reversal Agent to REGN5381 for reversal agent in healthy volunteers; Bispecific antibody targeting BCMA and CD3 for transplant desensitization in patients with chronic kidney disease; Bispecific antibody targeting MUC16 and CD28 for platinum-resistant ovarian cancer; Bispecific antibody targeting PSMA and CD28 for prostate cancer; Bispecific antibody targeting CD22 and CD28 for B-NHL; Antibody to GITR for solid tumors; Bispecific antibody targeting EGFR and CD28 for solid tumors; Antibody to IL2Rg for aplastic anemia; Antibody to Factor XI for thrombosis; Antibody to TMPRSS6 for transfusion dependent iron overload; Antibody to Factor XI for thrombosis; RNAi therapeutic targeting HSD17B13 for nonalcoholic steatohepatitis ("NASH") (ALN-HSD); Antibody to PD-1 Neoadjuvant CSCC; for second-line cervical cancer, ISA101b combination (CEMIPLIMAB); Antibody to IL-4R alpha subunit for ulcerative colitis; Eosinophilic gastroenteritis (Phase 2/3) (DUPILUMAB); Antibody to LAG-3 for first-line advanced NSCLC (Phase 2/3) (pivotal study) (FI-ANLIMAB); Bispecific antibody targeting BCMA and CD3 for multiple myeloma (pivotal study) (LINVOSELTA-MAB); Agonist antibody to leptin receptor ("LEPR") for generalized lipodystrophy; Partial lipodystrophy (MIBA-VADEMAB); Bispecific antibody targeting CD20 and CD3 for B-cell non-Hodgkin lymphoma ("B-NHL") (pivotal study) (ODRONEXTAMAB); Antibody to C5; studied as monotherapy and in combination with cemdisiran for CD55-deficient protein-losing enteropathy ("CHAPLE"), monotherapy (potentially pivotal study) (POZELIMAB); Agonist Antibody to NPR1/Reversal Agent to REGN5381 for heart failure; Antibody to IL-6R for polyarticular-course juvenile idiopathic arthritis ("pcJIA") (pivotal study); systemic juvenile idiopathic arthritis ("sJIA") (pivotal study) (SARILUMAB); Bispecific antibody targeting MUC16 and CD3 for platinum-resistant ovarian cancer (UBAMATAMAB); Immune activator targeting TLR9 for solid tumors (VIDUTOLIMOD); VEGF-Trap for Wet AMD, DME (AFLIBERCEPT); Antibody to PCSK9 for HeFH in pediatrics (ALIROCUMAB); Antibody to PD-1 for adjuvant CSCC (CEMIPLIMAB); Antibody to IL-4R alpha subunit for EoE in pediatrics; chronic obstructive pulmonary disease ("COPD"); bullous pemphigoid; chronic spontaneous urticaria ("CSU"); chronic pruritis of unknown origin (DUPILUMAB); Antibody to LAG-3 for first-line metastatic melanoma; First-line adjuvant melanoma (FIANLIMAB); Antibody to Activin A for fibrodysplasia ossificans progressiva ("FOP") (GARETOSMAB); Antibody to IL-33 for COPD (ITEPEKIMAB); Antibody to C5; studied as monotherapy and in combination with cemdisiran for myasthenia gravis, cemdisiran combination; paroxysmal nocturnal hemoglobinuria ("PNH"), cemdisiran combination (POZELIMAB); Multi-antibody therapy to Bet v 1 for birch allergy.

The description above and examples are illustrative, and are not intended to be restrictive. One of ordinary skill in the art may make numerous modifications and/or changes without departing from the general scope of the invention. For example, and as has been referenced, the above-described embodiments (and/or aspects thereof) may be used in combination with each other. Additionally, portions of the above-described embodiments may be removed without departing from the scope of the invention. In addition, modifications may be made to adapt a particular situation or aspect to the teachings of the various embodiments without departing from their scope. Many other embodiments will also be apparent to those of skill in the art upon reviewing the above description. Moreover, the features of any embodiment may be used in conjunction with any of the other disclosed embodiments.

Embodiments of the present disclosure may include the following features:

Item 1. A packaging comprising:
a tray having a body surrounding an exposed cavity and a groove;
a lip surrounding the opening, wherein the lip extends radially outward from the cavity and defines a periphery of the tray;
a retainer for covering a portion of the opening of the tray, the retainer having an aperture, wherein the aperture corresponds to the groove of the tray;
a removable cover; and
an auto-injector contained within the cavity, wherein the auto-injector is pre-filed with a medicament or other fluid.

Item 2. The packaging of item 1, further comprising a gaseous sterilant.

Item 3. The packaging of item 2, wherein the gaseous sterilant includes one or more of ethylene oxide, vaporized hydrogen peroxide, ethyl alcohol, nitrous oxide, or nitrogen dioxide.

Item 4. The packaging of item 1, wherein the tray includes a first plurality of sidewalls and a second plurality of sidewalls.

Item 5. The packaging of item 1, further comprising a lug.

Item 6. The packaging of item 1, wherein the lip includes an adhesive and forms a seal with the retainer to enclose the auto-injector within the cavity.

Item 7. The packaging of item 1, wherein the tray and/or the retainer includes one or more of polypropylene, polystyrene, polyethylene, polycarbonate, polyvinyl chloride, or polyethylene terephthalate glycol.

Item 8. The packaging of item 1, wherein the removable cover includes high-density polyethylene fibers, thermoplastic materials, or a combination thereof.

Item 9. The packaging of item 1, wherein the medicament or fluid comprises one or more of dupilumab and cemiplimab.

Item 10. A packaging for an auto-injector, the packaging comprising:
a tray having an opening and a cavity;
a lip surrounding the opening, wherein the lip extends radially outward from the cavity and defines a periphery of the tray;
a removable cover having a periphery that is adhered to the lip; and
a retainer for covering a portion of the opening of the tray.

Item 11. The packaging of item 10, wherein the removable cover is permeable to a gaseous sterilant.

Item 12. The packaging of item 10, wherein the gaseous sterilant includes one or more of ethylene oxide, vaporized hydrogen peroxide, ethyl alcohol, nitrous oxide, or nitrogen dioxide.

Item 13. The packaging of item 10, wherein the tray and/or the retainer includes one or more of polypropylene, polystyrene, polyethylene, polycarbonate, polyvinyl chloride, or polyethylene terephthalate glycol.

Item 14. The packaging of item 10, wherein the removable cover includes high-density polyethylene fibers, thermoplastic materials, or a combination thereof.

Item 15. The packaging of item 10, wherein the auto-injector contains a medicament comprising one or more of dupilumab and cemiplimab.

Item 16. A method of removing an externally-sterilized auto-injector from a packaging, the packaging including a tray having an opening and a cavity, a retainer, a removable cover, and a gaseous sterilant, the method comprising:
removing the removable cover to expose the retainer;
removing the retainer to expose the cavity of the tray;
grasping a portion of the externally-sterilized auto-injector held within the cavity of the tray; and
ejecting the externally-sterilized auto-injector from the tray.

Item 17. The method of item 16, further comprising pushing a portion of the tray towards the cavity of the tray, wherein pushing the portion of the tray causes a portion of the tray to flex.

Item 18. The method of item 17, wherein pushing the portion of the tray causes the externally-sterilized auto-injector to release from the cavity of the tray.

Item 19. The method of item 18, wherein the gaseous sterilant includes one or more of ethylene oxide, vaporized hydrogen peroxide, ethyl alcohol, nitrous oxide, or nitrogen dioxide.

Item 20. The method of item 19, wherein the externally-sterilized auto-injector contains a medicament comprising one or more of dupilumab and cemiplimab.

What is claimed is:
1. A packaging comprising:
a tray having a body surrounding an exposed cavity, an opening and a groove;

a lip surrounding the opening, wherein the lip extends radially outward from the cavity and defines a periphery of the tray;

a retainer for covering a portion of the opening of the tray, the retainer having an aperture, wherein the aperture corresponds to the groove of the tray;

a removable cover; and an auto-injector contained within the cavity, wherein the auto-injector is pre-filed with a medicament or other fluid.

2. The packaging of claim 1, further comprising a gaseous sterilant.

3. The packaging of claim 2, wherein the gaseous sterilant includes one or more of ethylene oxide, vaporized hydrogen peroxide, ethyl alcohol, nitrous oxide, or nitrogen dioxide.

4. The packaging of claim 1, wherein the tray includes a first plurality of sidewalls and a second plurality of sidewalls.

5. The packaging of claim 1, further comprising a lug.

6. The packaging of claim 1, wherein the lip includes an adhesive and forms a seal with the retainer to enclose the auto-injector within the cavity.

7. The packaging of claim 1, wherein the tray and/or retainer includes one or more of polypropylene, polystyrene, polyethylene, polycarbonate, polyvinyl chloride, or polyethylene terephthalate glycol.

8. The packaging of claim 1, wherein the removable cover includes high-density polyethylene fibers, thermoplastic materials, or a combination thereof.

9. The packaging of claim 1, wherein the medicament or fluid comprises one or more of dupilumab and cemiplimab.

10. A packaging for an auto-injector, the packaging comprising:

a tray having an opening and a cavity;

a lip surrounding the opening, wherein the lip extends radially outward from the cavity and defines a periphery of the tray;

a removable cover having a periphery that is adhered to the lip; and a retainer for covering a portion of the opening of the tray.

11. The packaging of claim 10, wherein the removable cover is permeable to a gaseous sterilant.

12. The packaging of claim 10, wherein the gaseous sterilant includes one or more of ethylene oxide, vaporized hydrogen peroxide, ethyl alcohol, nitrous oxide, or nitrogen dioxide.

13. The packaging of claim 10, wherein the tray and/or the retainer includes one or more of polypropylene, polystyrene, polyethylene, polycarbonate, polyvinyl chloride, or polyethylene terephthalate glycol.

14. The packaging of claim 10, wherein the removable cover includes high-density polyethylene fibers, thermoplastic materials, or a combination thereof.

15. The packaging of claim 10, wherein the auto-injector contains a medicament comprising one or more of dupilumab and cemiplimab.

16. A method of removing an externally-sterilized auto-injector from a packaging, the packaging including a tray having an opening and a cavity, a retainer, a removable cover, and a gaseous sterilant, the method comprising:

removing the removable cover to expose the retainer;

removing the retainer to expose the cavity of the tray;

grasping a portion of the externally-sterilized auto-injector held within the cavity of the tray; and ejecting the externally-sterilized auto-injector from the tray.

17. The method of claim 16, further comprising pushing a portion of the tray towards the cavity of the tray, wherein pushing the portion of the tray causes a portion of the tray to flex.

18. The method of claim 17, wherein pushing the portion of the tray causes the externally-sterilized auto-injector to release from the cavity of the tray.

19. The method of claim 18, wherein the gaseous sterilant includes one or more of ethylene oxide, vaporized hydrogen peroxide, ethyl alcohol, nitrous oxide, or nitrogen dioxide.

20. The method of claim 19, wherein the externally-sterilized auto-injector contains a medicament comprising one or more of dupilumab and cemiplimab.

* * * * *